United States Patent
Yang et al.

(10) Patent No.: US 10,329,570 B2
(45) Date of Patent: Jun. 25, 2019

(54) ANTAGONISTIC PD-1 APTAMER AND ITS APPLICATIONS IN CANCER THERAPY RELATED APPLICATIONS

(71) Applicants: Academia Sinica, Taipei (TW); National Taiwan University, Taipei (TW)

(72) Inventors: Pan-Chyr Yang, Taipei (TW); Yi-Chung Chang, Taipei (TW); Wei-Yun Lai, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 0 days.

(21) Appl. No.: 15/500,354

(22) PCT Filed: Jul. 31, 2015

(86) PCT No.: PCT/US2015/043162
§ 371 (c)(1),
(2) Date: Jan. 30, 2017

(87) PCT Pub. No.: WO2016/019270
PCT Pub. Date: Feb. 4, 2016

(65) Prior Publication Data
US 2017/0218369 A1 Aug. 3, 2017

Related U.S. Application Data

(60) Provisional application No. 62/031,427, filed on Jul. 31, 2014.

(51) Int. Cl.
| | | |
|---|---|---|
| C12N 15/11 | (2006.01) | |
| C12N 15/115 | (2010.01) | |
| A61K 31/7088 | (2006.01) | |
| C12N 15/113 | (2010.01) | |
| A61K 31/713 | (2006.01) | |
| C12N 15/117 | (2010.01) | |
| A61K 47/60 | (2017.01) | |

(52) U.S. Cl.
CPC ........ *C12N 15/115* (2013.01); *A61K 31/7088* (2013.01); *A61K 31/713* (2013.01); *A61K 47/60* (2017.08); *C12N 15/117* (2013.01); *C12N 15/1138* (2013.01); *C12N 2310/16* (2013.01); *C12N 2310/17* (2013.01); *C12N 2310/351* (2013.01)

(58) Field of Classification Search
CPC ............................ C12N 15/113; C12N 2310/16
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 2004/0241651 A1* | 12/2004 | Olek | C07K 14/4703 |
| | | | 435/6.16 |
| 2005/0159351 A1 | 7/2005 | Grate et al. | |
| 2009/0221680 A1* | 9/2009 | Diener | C12N 15/115 |
| | | | 514/44 R |
| 2009/0306179 A1* | 12/2009 | Bhanot | C12N 15/1137 |
| | | | 514/44 A |
| 2013/0209514 A1* | 8/2013 | Gilboa | A61K 39/0011 |
| | | | 424/277.1 |
| 2014/0148503 A1* | 5/2014 | Giangrande | A61K 48/0025 |
| | | | 514/44 R |
| 2015/0099791 A1* | 4/2015 | Krieg | C12N 15/113 |
| | | | 514/44 A |
| 2017/0204407 A1* | 7/2017 | Gilbert | C12N 15/1079 |

FOREIGN PATENT DOCUMENTS

| | | | | |
|---|---|---|---|---|
| WO | WO-9731012 A1 * | 8/1997 | ............. | C12N 15/10 |
| WO | WO 2004/047742 A2 | 6/2004 | | |
| WO | WO 2004/094614 A2 | 11/2004 | | |
| WO | WO 2010/144295 A1 | 12/2010 | | |
| WO | WO 2013/142255 A2 | 9/2013 | | |
| WO | WO 2014/082083 A1 | 5/2014 | | |

OTHER PUBLICATIONS

Govan et al., Stabilization and photochemical regulation of antisense agents through PEGylation, 2011, Bioconjugate Chemistry, vol. 22, pp. 2136-2142.*
Homo sapines CaM kinase like vesicle associated (CAMKV), transcript variant 1, mRNA, Sequence ID: NM_0204046.4, retrieved from www.ncbi.nlm.gov on Nov. 6, 2017.*
Homo sapiens protein S, alpha (PROS1), transcript variant 1, mRNA, Sequence ID:NM_001314077.1, retrieved from www.ncbi.nlm.gov on Nov. 6, 2017.*
Homo sapiens IBA57 homolog, iron-sulfur cluster assembly (IBA57), transcript variant 1, mRNA, Sequence ID: NM_001010867.3, retrieved from www.ncbi.nlm.gov on Nov. 6, 2017.*
Mus musculus transmembrane protein 248 (Tmem248), transcript variant 1, mRNA, Sequence ID: NM_027854.1, retrieved from www.ncbi.nlm.gov on Nov. 6, 2017.*
Iversen et al., Optimized siRNA-PEG conjugates for extended blood circulation and reduced urine excretion in mice, 2013, Theranostics, vol. 3, pp. 201-209.*
Jäschke et al., Synthesis and properties of oligodeoxyribonucleotide-polyethylene glycol conjugates, 1994, Nucleic Acids Research, vol. 22, pp. 4810-4817.*
Zhao et al., Delivery of G3139 using releasable PEG-linkers: Impact on pharmacokinetic profile and anti-tumor efficacy, 2007, Journal of Controlled Release, vol. 119, pp. 143-152.*

(Continued)

*Primary Examiner* — Dana H Shin
(74) *Attorney, Agent, or Firm* — Wolf, Greenfield & Sacks, P.C.

(57) ABSTRACT

Aptamers that bind to and antagonize programmed cell death protein 1 (PD-1). Also provided herein are pharmaceutical compositions comprising such anti-PD-1 aptamers and methods for using the same for promoting T cell proliferation, treating cancer or infectious diseases, such as human immunodeficiency virus (HIV) infection.

31 Claims, 23 Drawing Sheets

Specification includes a Sequence Listing.

(56) References Cited

OTHER PUBLICATIONS

Bailon et al., PEG+modified biopharmaceuticals, 2009, Expert Opinion on Drug Delivery, vol. 6, pp. 1-16.*
*Homo sapiens* RNA binding protein, mRNA processing factor 2 (RBPMS2), transcript variant 1, mRNA, NCBI reference sequence: NM_194272.2,accessed and retrieved from www.ncbi.nlm.nih.gov on Oct. 2, 2018. (Year: 2018).*
*Homo sapiens* kyphoscoliosis peptidase (KY), transcript variant 3, mRNA, NCBI reference sequence: NM_001350860.1, accessed and retrieved from www.ncbi.nlm.nih.gov on Oct. 2, 2018. (Year: 2018).*
*Homo sapiens* CaM kinase like vesicle associated (CAMKV), transcript variant 1, mRNA, NCBI reference sequence: NM_024046.4, accessed and retrieved from www.ncbi.nlm.nih.gov on Oct. 2, 2018. (Year: 2018).*
*Homo sapiens* protein S (PROS1), transcript variant 1, mRNA, NCBI reference sequence: NM_001314077.1, accessed and retrieved from www.ncbi.nlm.nih.gov on Oct. 2, 2018. (Year: 2018).*
Mus musculus whirlin (Whrn), transcript variant 1, mRNA, NCBI reference sequence: NM_028640.2, accessed and retrieved from www.ncbi.nlm.nih.gov on Oct. 2, 2018. (Year: 2018).*
Mus musculus junctophilin 4 (Jph4), mRNA, NCBI reference sequence: NM_177049.5, accessed and retrieved from www.ncbi.nlm.nih.gov on Oct. 2, 2018. (Year: 2018).*
Eppstein et al., Biological activity of liposome-encapsulated murine interferon gamma is mediated by a cell membrane receptor. Proc Natl Acad Sci U S A. Jun. 1985;82(11):3688-92.
Gilboa et al., Use of oligonucleotide aptamer ligands to modulate the function of immune receptors. Clin Cancer Res. Mar. 1, 2013;19(5):1054-62. doi: 10.1158/1078-0432.CCR-12-2067.
Hwang et al., Hepatic uptake and degradation of unilamellar sphingomyelin/cholesterol liposomes: a kinetic study. Proc Natl Acad Sci U S A. Jul. 1980;77(7):4030-4.
McNamara et al., Multivalent 4-1BB binding aptamers costimulate CD8+ T cells and inhibit tumor growth in mice. J Clin Invest. Jan. 2008;118(1):376-86.
PCT/US2015/043162, Sep. 25, 2015, International Search Report and Written Opinion.
PCT/US2015/043162, Feb. 9, 2017, International Preliminary Report on Patentability.

\* cited by examiner

A

B

C

D

ANTAGONISTIC PD-1 APTAMER AND ITS APPLICATIONS IN CANCER THERAPY RELATED APPLICATIONS

CROSS-REFERENCE TO RELATED APPLICATIONS

The present application is a national stage filing under 35 U.S.C. § 371 of International Application No. PCT/US2015/043162, filed Jul. 31, 2015, which claims priority under 35 U.S.C. § 119(e) to U.S. Provisional Application No. 62/031,427, filed Jul. 31, 2014, the entire content of each of which is incorporated by reference herein in its entirety.

BACKGROUND OF INVENTION

Cancer cells may regulate host immune system to evade from immune surveillance. Several approaches had been developed to reactivate the immune system in tumor microenvironment and restore T cell ability to eradicate cancer cells. One of these approaches is immune-checkpoint targeting based on blocking the receptors that normally inhibit the immune response, such as Cytotoxic T-Lymphocyte Antigen 4 (CTLA-4) and Programmed death 1 (PD1). Ipilimumab, an antagonistic antibody (mAb) against CTLA-4, was approved for the treatment of advanced melanoma in 2011 by FDA. Recently, inhibitory antibody against PD-1 was proved in clinical trial to be effectively in treatment of melanoma and non-small-cell lung cancer (NSCLC).

PD-1 is named for its highly express on dying cells and involve in the process of program cell death. PD-1 is a type I transmembrane protein containing extracellular domain belongs to immunoglobulin superfamily and intracellular domain containing an immunoreceptor tyrosine-based inhibitory motif (ITIM). Similar to CTLA-4 receptor, PD-1 is also a powerful inhibitory receptor that inhibits T cell activation. However the signaling pathway analysis reveals that PD-1 and CTLA-4 inhibit T cell activation by distinct mechanism and dual treatment of CTLA-4 and PD-1 antagonistic antibody can induce a synergistic effect. Moreover, compare to CTLA-4 that only express on T cell, PD-1 majorly express on activated T cell, B cell and macrophage. The boarder distribution of PD-1 receptor suggests it might be involved in more widely role in immune regulation. All these finding indicated that molecules which capable to block PD-1 pathway might hold a great potential in anti-cancer immunotherapy.

Aptamers are short DNA or RNA molecules that are capable of forming secondary structure or even complex three-dimensional structures. Aptamer technology has progressed tremendously since its discovery in the early 1990s. Aptamers have several advantages that make it suitable for therapeutic application, including lower molecular weight that allows it easier to penetrate through tissue than antibody, low cost in chemical synthesis, established modification methods and high stability. It is therefore of great interest to develop suitable aptamers having high affinity to a target protein.

SUMMARY OF INVENTION

The present disclosure is based on the development of a number of anti-PD-1 nucleic acid aptamers, which successfully increased T cell proliferation in vitro and suppressed tumor growth in vivo.

Accordingly, one aspect of the present disclosure features a nucleic acid aptamer that binds PD-1 and neutralizes the inhibitory activity of PD-1 (anti-PD-1 aptamer). The anti-PD-1 aptamer may comprise the nucleic acid sequence CCATCTCCC (SEQ ID NO: 1), TATATTGTWC (SEQ ID NO: 2), GTACAGTTX (SEQ ID NO: 3), GCACTACA (SEQ ID NO: 4), GTACATCAY (SEQ ID NO: 5), YGCTACTGTZ (SEQ ID NO: 6), or CCATCTCCCGTCC (SEQ ID NO: 7). In each of the sequences where applicable, W is C or G, X is C, A, or is absent, Y is A, T, or is absent, and/or Z is T, C, or is absent. In some embodiments, the anti-PD-1 aptamer disclosed herein binds to PD-1 with a dissociation constant ($K_d$) lower than 20 nM.

In some embodiments, the nucleic acid aptamer is conjugated with polyethylene glycol (PEG). In some examples, the PEG is conjugated to the 3' end of the nucleic acid aptamer. Alternatively or in addition, the PEG moiety may have a molecular weight ranging from 10 kDa to 30 kDa. For example, the PEG moiety may have a molecular weight of 20 kDa.

In another aspect, the present disclosure provides an anti-PD-1 aptamer dimer, comprising a first anti-PD-1 aptamer, a second anti-PD-1 aptamer, and a polymer moiety that links the first anti-PD-1 aptamer and the second anti-PD-1 aptamer. The first and second anti-PD-1 aptamers may be any aptamer provided herein. In some examples, the first and second anti-PD-1 aptamers can be identical. In other examples, they can be different. As one example, the first and second anti-PD-1 aptamers both comprise the nucleic acid sequence of SEQ ID NO: 1.

In any of the anti-PD-1 aptamer dimers described herein, the polymer moiety that links the first and second anti-PD-1 aptamers can be PEG, which may have a molecular weight ranging from 10 kDa to 30 kDa, e.g., 20 kDa. The first aptamer, the second aptamer, or both, in some instances, may be linked to the polymer moiety (e.g., PEG) via a linker. In some examples, the linker is a polyT fragment, which may contain 5 to 20 thymine (T) residues.

In some embodiments, the anti-PD-1 aptamer comprises a nucleic acid sequence that is at least 85% (e.g., 90% or 95%) identical to (i) CTTCCATCTCCCATGCTTAGTCAAACATAC (SEQ ID NO: 8); or (ii) TGATCACAAGAATAACTATCCCATCTCCCT (SEQ ID NO: 9). In one example, the aptamer comprises the nucleic acid sequence of (i) CTTCCATCTCCCATGC TTAGTCAAACATAC (SEQ ID NO: 8); or (ii) TGATCACAAGAATAACTATCCCATCT CCCT (SEQ ID NO: 9). In another example, aptamer is (i) TCCCTACGGCGCTAACCTTCCAT CTCCCATGCTTAGTCA AACATACGCCACCGTGCTACAAC (SEQ ID NO: 10); (ii) TCCCTACGGCGCTAACTGATCACAAGAATAACTATCCCATCTCCCTGCCACCGTG CTACAAC (SEQ ID NO: 11); or TCCCTACGGCGCTAACCCTCCCCTAGTATATATTGTCCTCGTCTATGCCACCGTGCTACAAC (SEQ ID NO: 12).

Another aspect of the present disclosure features a pharmaceutical composition, comprising any of the anti-PD-1 aptamers described herein or any of the anti-PD-1 aptamer dimers described herein and a pharmaceutically acceptable carrier.

In yet another aspect, the present disclosure provides a method for treating cancer (e.g., melanoma, non-small cell lung cancer, colorectal cancer, or renal-cell cancer). The method comprises administering to a subject in need thereof an effective amount of any of the pharmaceutical compositions described herein, which comprises at least one anti-PD-1 nucleic acid aptamer as also described herein. In some embodiments, the subject is a human patient having, suspected of having, or at risk for cancer.

Further, the present disclosure provides a method of enhancing immune activity in a subject, the method comprising administering to a subject in need thereof an effective amount (e.g., effective in increasing T cell activation) of any of the anti-PD-1 aptamer-containing pharmaceutical composition as described herein. The subject may be a human patient having, suspected of having, or at risk for cancer (e.g., melanoma, non-small cell lung cancer, colorectal cancer, or renal-cell cancer). Alternatively, the subject may be a human patient having or suspected of having HIV infection.

Also within the scope of the present disclosure are (a) pharmaceutical compositions for use in treating cancer (e.g., lung cancer, melanoma, colorectal cancer, or renal-cell cancer) or an infectious disease such as HIV infection, wherein the pharmaceutical composition comprises an anti-PD-1 nucleic acid aptamer, an anti-PD-1 aptamer dimer, or a PEG conjugate thereof as described herein, e.g., a nucleic acid comprising the nucleic acid sequence of CCATCTCCC (SEQ ID NO: 1) or others described herein, and a pharmaceutically acceptable carrier; and (b) use of the anti-PD-1 aptamer, the anti-PD-1 aptamer dimer, and/or a PEG conjugate thereof for manufacturing a medicament for treating cancer (e.g., lung cancer, melanoma, colorectal cancer, or renal-cell cancer) or an infectious disease such as HIV infection.

The details of one or more embodiments of the invention are set forth in the description below. Other features or advantages of the present invention will be apparent from the following drawings and detailed description of several embodiments, and also from the appended claims.

DETAILED DESCRIPTION OF INVENTION

Figure 1:
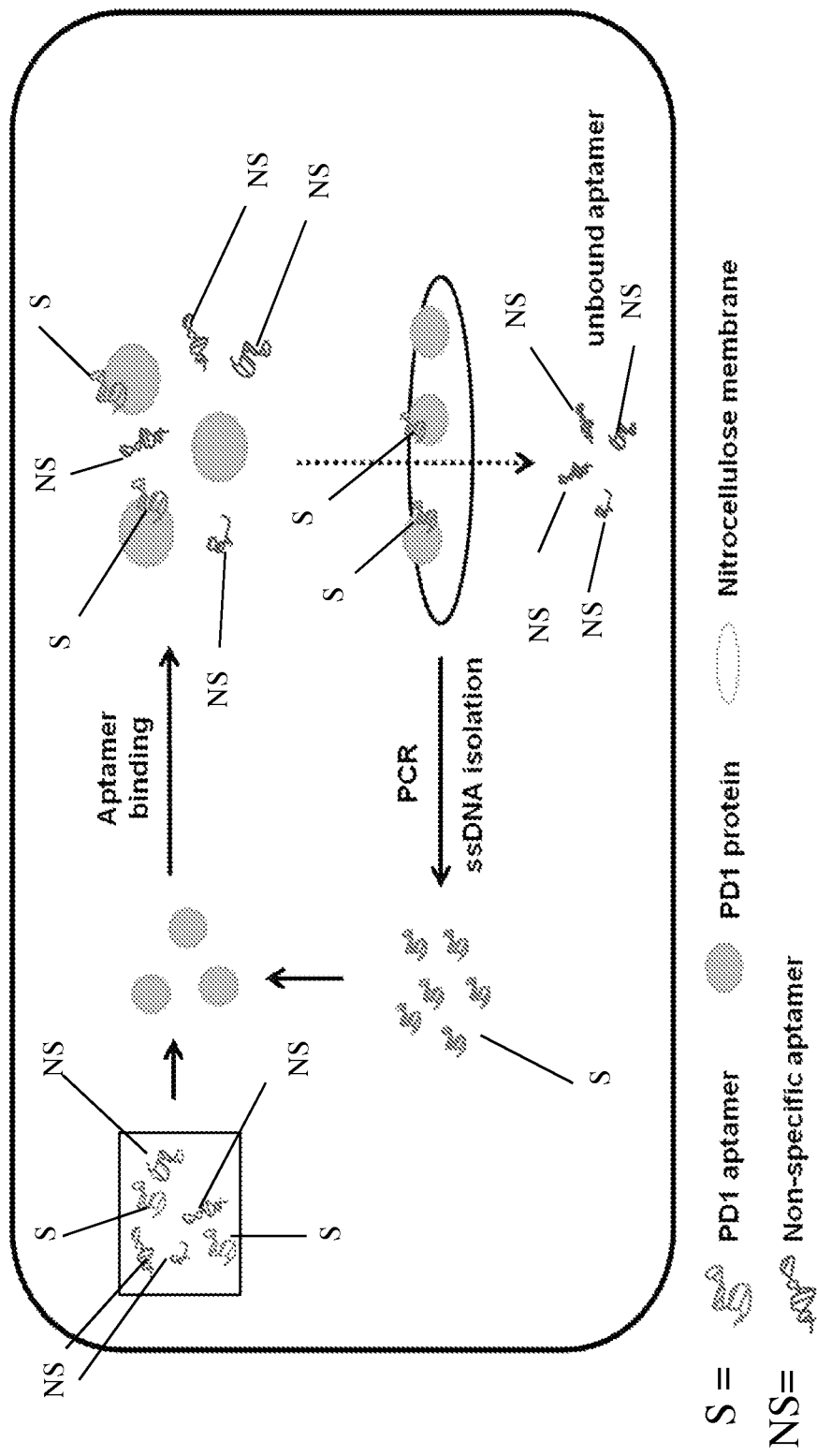
FIG. 1 is a schematic illustration showing the process of selecting nucleic acid aptamers binding to PD-1 via SELEX. In the schematic "S" indicates a PD1 specific aptamer and "NS" indicates a non-specific aptamer.

The present disclosure is based on the development of a number of anti-PD-1 nucleic acid aptamers and the successful enhancement of T cell proliferation by exemplary anti-PD-1 aptamers. Results show that, surprisingly, aptamer (e.g., PD7) treatment resulted in (i) a stronger effect on T cell proliferation (e.g., CD+ T cell proliferation) than a PD-1 antagonistic antibody, and (ii) a marked reduction in tumor growth in both syngeneic and humanized mouse tumor models. Further, results showed that aptamer treatment prevented binding between PD-1 and PDL-1. Thus, anti-PD-1 aptamers such as those described herein would be effective in enhancing immune activity and preventing tumor growth, thereby effective in treating diseases such as cancer and infectious diseases (e.g., HIV infection).

Accordingly, described herein are anti-PD-1 aptamers, pharmaceutical compositions comprising such, and methods for enhancing immune activity and/or treating diseases such as cancer and HIV infection with the anti-PD-1 aptamers disclosed herein.

Anti-PD-1 Aptamers

Described herein are nucleic acid aptamers that bind to PD-1 and inhibits it activity (anti-PD-1 aptamers), thereby enhancing immune activity such as T cell activity. A nucleic acid aptamer as used herein refers to a nucleic acid molecule (DNA or RNA) having a binding activity for a particular target molecule (e.g., PD-1). The aptamer can inhibit the activity of a particular target molecule by binding to the particular target molecule. The anti-PD-1 aptamer of the present disclosure, in linear or circular form, may be an RNA, a DNA (e.g., a single-stranded DNA), a modified nucleic acid, or a mixture thereof. The anti-PD-1 aptamers may be non-naturally molecules (e.g., containing a nucleotide sequence not existing in native genes or containing modified nucleotides not existing in nature). Alternatively or in addition, the anti-PD-1 aptamers may not contain a nucleotide sequence that encodes a functional peptide.

PD-1, referring to programmed cell death protein 1 (also known as CD279), is a cell surface protein expressed on T cells and pro-B cells. It plays a role in T cell and B cell death and differentiation. In humans, PD-1 is encoded by the PDCD1 gene. The amino acid sequence of human PD-1 can be found under GenBank accession number NP_005009.

The anti-PD-1 nucleic acid aptamer disclosed herein may comprise the nucleotide sequence of CCATCTCCC (SEQ ID NO: 1); TATATTGTWC (SEQ ID NO: 2), in which W is C or G; GTACAGTTX (SEQ ID NO: 3), in which X is C, A, or absent; GCACTACA (SEQ ID NO: 4); GTACATCAY (SEQ ID NO: 5), in which Y is A, T, or absent; YGCTACTGTZ (SEQ ID NO: 6), in which Y is A, T or absent, and Z is T, C, or absent; or CCATCTCCCGTCC (SEQ ID NO: 7). Other examples of anti-PD-1 aptamers are provided in FIG. 3, panel B.

In some embodiments, the anti-PD-1 nucleic acid aptamer disclosed herein may comprise a nucleotide sequence at least 85% (e.g., 90%, 95%, or 98%) identical to 5'-CTTC-CATCTCCCATG CTTAGTCAAACATAC-3' (SEQ ID NO: 8), or 5'-TGATCACAAGAATAACTATCCCATCTCC CT-3' (SEQ ID NO: 9).

The "percent identity" of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, wordlength-12 to obtain nucleotide sequences homologous to the nucleic acid molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other embodiments, the anti-PD-1-4 aptamers described herein may contain up to 8 (e.g., up to 6, 5, 4, 3, 2, or 1) nucleotide variations as compared to the nucleotide sequence of 5'-CTTCCATCTCCCATGCTTAGT-CAAACATAC-3' (SEQ ID NO: 8), or 5'-TGATCA-CAAGAATA ACTATCCCATCTCCCT-3' (SEQ ID NO: 9). Positions where such variations can be introduced can be determined based on, e.g., the secondary structures of PD16 (SEQ ID NO: 11) and PD7 (SEQ ID NO:10), which comprise the reference nucleotide sequence (see FIG. 4B).

In some examples, the anti-PD-1 aptamers may contain primer site(s) at the 5' end, the 3' end, or both. In one example, the anti-PD-1 aptamer has the nucleotide sequence of (SEQ ID NO: 10)
5'-*TCCCTACGGCGCTAAC* CTTCCATCTCCCATGCTTAGTCAAACATAC *GCCACCGTGCTACAAC*-3', (SEQ ID NO: 11)
5'-*TCCCTACGGCGCTAAC* TGATCACAAGAATAACTATCCCATCTCCCT *GCCACCGTGCTACAAC*-3',
or (SEQ ID NO: 12)
5'-*TCCCTACGGCGCTAAC*CCTCCCCTAGTATATATTGTCCTCGTCTAT *GCCACCGTGCTA CAAC*-3' in which the underlined/italic flanking sequences refer to the 5' and 3' primer sites.

Any of the anti-PD-1 aptamers disclosed herein may contain up to 200 nucleotides (nts), e.g., 150 nts, 100 nts, 80 nts, 70 nts, 60 nts. 50 nts, 40 nts, or 30 nts. In some examples, the anti-PD-1 aptamer may contain nucleotides ranging from 30-150 nts, 30-100 nts, 30-80 nts, 30-70 nts, 30-60 nts, 30-50 nts, or 30-40 nts.

In some embodiments, the anti-PD-1 aptamers described herein may bind to PD-1 (e.g., human PD-1) with a dissociation constant (Kd) lower than 20 nM (e.g., 15 nM, 10 nM, 5 nm, 1 nm, or less). The anti-PD-1 aptamer may specifically bind human PD-1. Alternatively, the aptamer may bind to PD-1 molecules from different species (e.g., human and mouse). When binding to a PD-1 molecule expressed on T cell surface, such an aptamer may inhibit the activity of PD-1 (thus increase T cell activity) by at least 20% (e.g., 40%, 50%, 80%, 100%, 2-fold, 5-fold, 10-fold, 100-fold, or 1,000-fold). The inhibitory activity of an anti-PD-1 aptamer on PD-1 (and thus the activation in enhancing T cell activity) may be determined by, e.g., those described in the Examples below.

In some embodiments, the anti-PD-1 aptamers described herein may contain non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the aptamer described herein has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

In another example, the aptamers described herein include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted C1 to C10 alkyl or C2 to C10 alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

Alternatively or in addition, aptamers described herein include one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of aptamer molecules to their targeting sites. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the aptamers described herein can be prepared by conventional methods, e.g., chemical synthesis or in vitro transcription. Their intended bioactivity as described herein can be verified by, e.g., those described in the Examples below. Vectors for expressing any of the anti-PD-1 aptamers are also within the scope of the present disclosure.

Any of the aptamers described herein may be conjugated to one or more polyether moieties, such as polyethylene glycol (PEG) moieties, via covalent linkage, non-covalent linkage, or both. Accordingly, in some embodiments, aptamers described herein are pegylated. The disclosure is not meant to be limiting with respect to a PEG moiety of a specific molecular weight. In some embodiments, the polyethylene glycol moiety has a molecular weight ranging from 5 kDa to 100 kDa, 10 kDa to 80 kDa, 20 kDa to 70 kDa, 20 kDa to 60 kDa, 20 kDa to 50 kDa, 10 kDa to 40 kDa, 10 kDa to 30 kDa, or 15 kDa to 25 kDa. In some examples, the PEG moiety has a molecular weight of 20 kDa. The PEG moiety conjugated to the anti-PD-1 aptamer described herein can be linear or branched. It may be conjugated to the 5' end of the nucleic acid aptamer, the 3' end of the aptamer, or both. When needed, the PEG moiety can be conjugated to the 3' end of the nucleic acid aptamer covalently. In some embodiments, the nucleic aptamer comprises the nucleotide sequence CCATCTCCCA (SEQ ID NO: 13) or CCATCTCCATTTTTTTTTT (SEQ ID NO: 14). The polyT fragment in SEQ ID NO: 14 is a spacer and the length of this fragment may vary as known to those skilled in the art.

Methods for conjugating PEG moieties to nucleic acids are known in the art and have been described previously, for example, in PCT Publication No. WO 2009/073820 A2, the relevant teachings of which are incorporated by reference herein It should be appreciated that the PEG conjugated nucleic acid aptamers and methods for conjugating PEG to the nucleic acid aptamers described herein, are exemplary and not meant to be limiting.

The present disclosure also provides dimers of any of the anti-PD-1 nucleic acid aptamers described herein. In some embodiments, an anti-PD-1 aptamer dimer comprises two anti-PD-1 aptamers linked by a suitable polymer moiety, which can be a PEG moiety as those described herein. Either one or both of the two aptamers in a dimer may comprise a nucleotide sequence of any one of SEQ ID NOs: 1-14. The two anti-PD-1 aptamers may be identical or different. For example, one or both of the anti-PD-1 aptamers may comprise (SEQ ID NO: 13) or (SEQ ID NO: 14). In another example, the anti-PD-1 aptamer dimer as described herein may have one aptamer comprising (SEQ ID NO:1) and another aptamer comprising (SEQ ID NO: 2).

In some embodiments, the polymer moiety of any of the anti-PD-1 aptamer dimers provided herein is PEG, which may have a molecular weight as described herein.

In some embodiments, the anti-PD-1 aptamer dimers provided herein comprise aptamers that are linked to the polymer moiety via a linker. In one example, the first aptamer is linked to the polymer moiety via a linker. In another example, the second aptamer is linked to the polymer moiety via a linker. In yet another example, the first aptamer and the second aptamer is linked to the polymer moiety via a linker. A "linker" as used herein, refers to a chemical moiety linking two molecules or moieties. In some examples, the linker comprises one or more nucleotides, which may be deoxyribonucleotides. In some examples the nucleic linker is from 1 to 50 nucleotides in length. Such linkers may be from 1 to 5, from 1 to 10, from 1 to 15, from 1 to 20, from 1 to 30, from 1 to 40, from 10 to 15, from 10 to 20, from 10 to 30, from 10 to 40, from 10 to 50, from 20 to 30, from 20 to 40, from 20 to 50, from 30 to 40, from 30 to 50, or from 40 to 50 nucleotides in length. In some examples, the linker is 11 nucleotides in length. The linker may comprise adenine (A), cytosine (C), thymine (T) and/or guanine (G). In some examples, the linker comprises a polyT fragment. A "polyT fragment" refers to a stretch of 2 or more consecutive thymine (T) nucleotide residues. For example, the polyT linker may comprise from 2 to 50 T residues. In some examples, the polyT linker is from 2 to 40, from 2 to 35, from 2 to 30, from 2 to 25, from 2 to 20, from 5 to 15, or from 10 to 15 nucleotides in length. In some embodiments, the poly T linker comprises 11 consecutive thymine (T) nucleotides.

Pharmaceutical Compositions

One or more of the anti-PD-1 aptamers, the aptamer dimers, or PEG conjugates thereof as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS or polyethylene glycol (PEG).

In some examples, the pharmaceutical composition described herein comprises liposomes containing the PD-1 binding aptamers (or a vector for producing the aptamer), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-PD-1 aptamers as described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the PD-1 binding aptamer, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The pharmaceutical compositions to be used for in vivo administration must be sterile. This is readily accomplished by, for example, filtration through sterile filtration membranes. Therapeutic PD-1 binding aptamer compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an anti-PD-1 aptamer with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Methods of Treatment

Any of the anti-PD-1 aptamers, the dimers, or PEG conjugates thereof as described herein can be used to enhance immune activity, particularly promoting T cell prolifeartion, thereby effective in treating cancer or infectious diseases such as viral (e.g., HIV) infection or bacterial infection.

To practice the method disclosed herein, an effective amount of the pharmaceutical composition described herein that contains at least one anti-PD-1 aptamer can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-PD-1 aptamer-containing composition as described herein can be aerosolized using a fluorocarbon formulation and a metered dose inhaler, or inhaled as a lyophilized and milled powder.

As used herein, "an effective amount" refers to the amount of each active agent required to confer therapeutic effect on the subject, either alone or in combination with one or more other active agents. In some embodiments, the therapeutic effect is reduced tumor burden, reduction of cancer cells, or increased immune activity. Determination of whether an amount of the PD-1 binding aptamers achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a PD-1 binding aptamer may be appropriate. Various formulations and devices for achieving sustained release are known in the art.

In one example, dosages for an anti-PD-1 aptamer as described herein may be determined empirically in individuals who have been given one or more administration(s) of the PD-1 binding aptamer. Individuals are given incremental dosages of the antagonist. To assess efficacy of the antagonist, an indicator of the disease/disorder can be followed.

Generally, for administration of any of the anti-PD-1 aptamers described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the PD-1 binding aptamer, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the PD-1 binding aptamer used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a PD-1 binding aptamer as described herein will depend on the specific PD-1 binding aptamer, the type and severity of the disease/disorder, whether the PD-1 binding aptamer is administered for preventive or therapeutic purposes, previous therapy, the patient's clinical history and response to the antagonist, and the discretion of the attending physician. A clinician may administer a PD-1 binding aptamer, until a dosage is reached that achieves the desired result. In some embodiments, the desired result is a decrease in tumor burden, a decrease in cancer cells, or increased immune activity. Methods of determining whether a dosage resulted in the desired result would be evident to one of skill in the art. Administration of one or more PD-1 binding aptamers can be continuous or intermittent, depending, for example, upon the recipient's physiological condition, whether the purpose of the administration is therapeutic or prophylactic, and other factors known to skilled practitioners. The administration of a PD-1 binding aptamer may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the PD-1 binding aptamers described herein are administered to a subject in need of the treatment at an amount sufficient to reduce tumor burden or cancer cell growth, or HIV proliferation by at least 5% (e.g., 10%, 20%, 30%, 40%, 50%, 60%, 70%, 80%, 90% or greater) in vivo. In other embodiments, the PD-1 binding aptamers are administered in an amount effective in reducing the activity level of PD-1 by at least 5% (e.g., 10%, 20%, 30%, 40%, 50%, 60%, 70%, 80%, 90% or greater). In other embodiments, the PD-1 binding aptamers are administered in an amount effective in increasing immune activity by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble PD-1 binding aptamers can be administered by the drip method, whereby a pharmaceutical formulation containing the PD-1 binding aptamer and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the PD-14 binding aptamer, can be dissolved and administered in a pharmaceutical excipient such as Water-for-Injection, 0.9% saline, or 5% glucose solution.

In one embodiment, a PD-1 binding aptamer is administered via site-specific or targeted local delivery techniques. Examples of site-specific or targeted local delivery techniques include various implantable depot sources of the PD-1 binding aptamer or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., the PD-1 binding aptamers described herein or vectors for producing such) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The subject to be treated by the methods described herein can be a mammal, such as a farm animals, sport animals, pets, primates, horses, dogs, cats, mice and rats. In one example, the subject is a human. The anti-PD-1 aptamer-containing composition may be used for enhancing immune activity, for example, T cell activity, in a subject in need of the treatment. In some examples, the subject may be a human patient having, suspected of having, or at risk for a cancer, such as lung cancer, melanoma, colorectal cancer, or renal-cell cancer. In other examples, the subject can be a human patient having or suspected of having HIV infection. Such a patient can also be identified by routine medical practices.

A subject having a target disease or disorder (e.g., cancer or viral infection such as HIV infection, or bacterial infection) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

The particular dosage regimen, i.e., dose, timing and repetition, used in the method described herein will depend on the particular subject (e.g., a human patient) and that subject's medical history.

In some embodiments, the anti-PD-1 aptamer may be co-used with another suitable therapeutic agent (e.g., an anti-cancer agent or an anti-HIV agent). Alternatively or in addition, the anti-PD-1 aptamer may also be used in conjunction with other agents that serve to enhance and/or complement the effectiveness of the agents.

Treatment efficacy for a target disease/disorder can be assessed by, e.g., a method described in the Examples below.

Kits for Use in Alleviating a Target Disease

The present disclosure also provides kits for use in enhancing immune activity (e.g., T cell activity), alleviating cancer (e.g., lung cancer, melanoma, colorectal cancer, or renal-cell cancer), and/or treating or reducing the risk for HIV infection. Such kits can include one or more containers comprising an aptamer that binds PD-1, e.g., any of those described herein.

In some embodiments, the kit can comprise instructions for use in accordance with any of the methods described herein. The included instructions can comprise a description of administration of the aptamer to treat, delay the onset, or alleviate a target disease as those described herein. The kit may further comprise a description of selecting an individual suitable for treatment based on identifying whether that individual has the target disease. In still other embodiments, the instructions comprise a description of administering the aptamer to an individual at risk of the target disease.

The instructions relating to the use of a PD-1 binding aptamer generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with cancer, such as those described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a PD-1 binding aptamer as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Identification of Anti-PD-1 Aptamers Via SELEX

Figure 2:
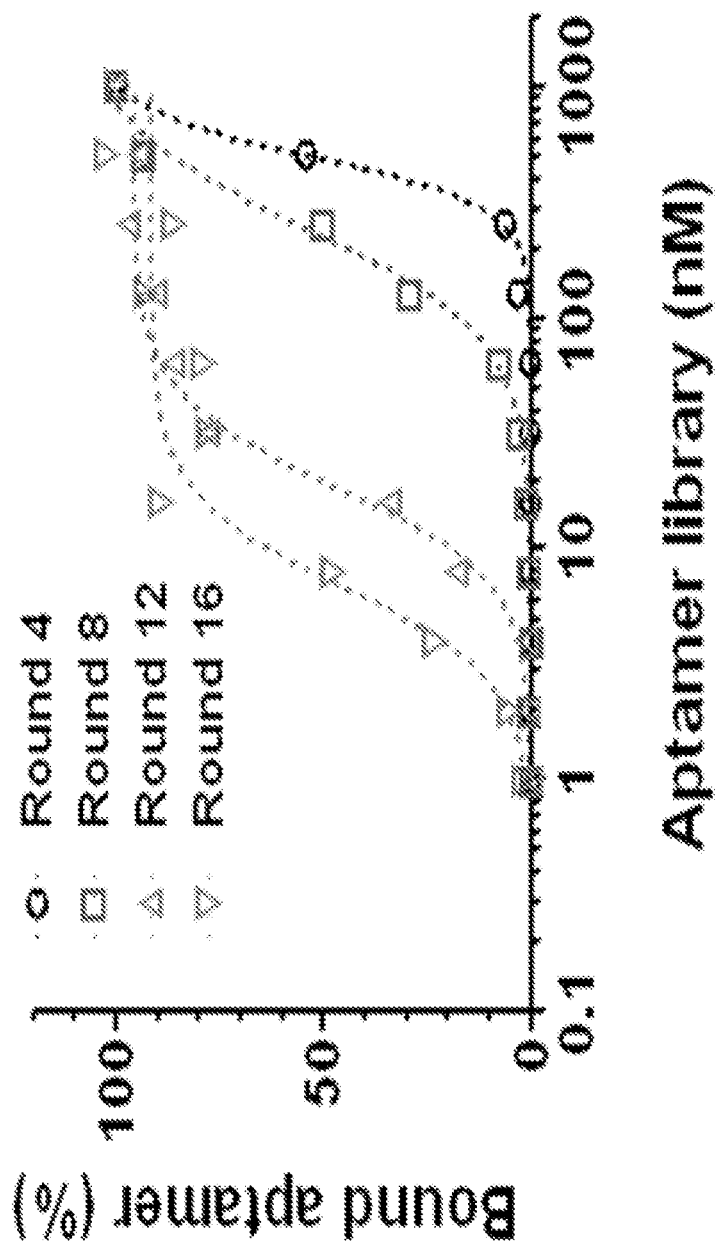
FIG. 2 is a chart showing affinity analysis of aptamer pools obtained from different rounds of SELEX screening as indicated.

PD1 extracellular domain was used in the selection to reduce the number of nonspecific aptamer. The SELEX strategy we use here is membrane SELEX as illustrated in FIG. 1. Briefly, the PD1 proteins were first incubated with aptamer library and the flow through a nitrocellulose membrane by vacuum aspiration. After several times of washing, the PD1 bounded aptamer will be trapped on membrane and further amplified by PCR reaction. The new aptamer pool composed of single strand aptamer will be isolated from PCR product and incubation with new batch of PD1 protein to start a new round of SELEX. For showing the successful evolution of aptamer pools, aptamer pools from round 4, 8, 12, and 16 of PD1 selection were selected and analyzed. The binding affinity and specificity were measured by total binding assay coupled with RT-qPCR (FIG. 2). These data indicated that the affinity were elevated along with the increase of SELEX rounds. For example, the affinity increased from 120.7 nM (Round 4) to 6.6 nM (Round 16) (FIG. 2). These data suggested that our SELEX procedure worked efficiently in selecting high affinity and specific aptamers. After 16 rounds of selection, the aptamer pools were sequenced.

Example 2: Affinity Analysis of Aptamer Pools from Different SELEX Rounds

Aptamer pools in round 4, 8, 12, and 16 against PD-1 were amplified and follow by 2 fold of serial dilution which started from 500 nM. Ten dosage points were analyzed for each of the selected pool by incubation with PD-1 proteins. The bounded aptamers were isolated by cellulose membrane binding and quantified by RT-qPCR. The result was shown in XY plot. The black circle indicated the result for round 4, green square for round 8, blue triangle for round 12 and red inverted triangle for round 16. The dashed line indicated the fit curves for each of the pools. The dissociation constant for round 4, 8, 12, 16 were 493.7 nM, 245.7 nM, 18.5 nM and 6.8 nM, respectively.

Example 3: Sequence Analysis of PD1 Aptamers

Figure 3:
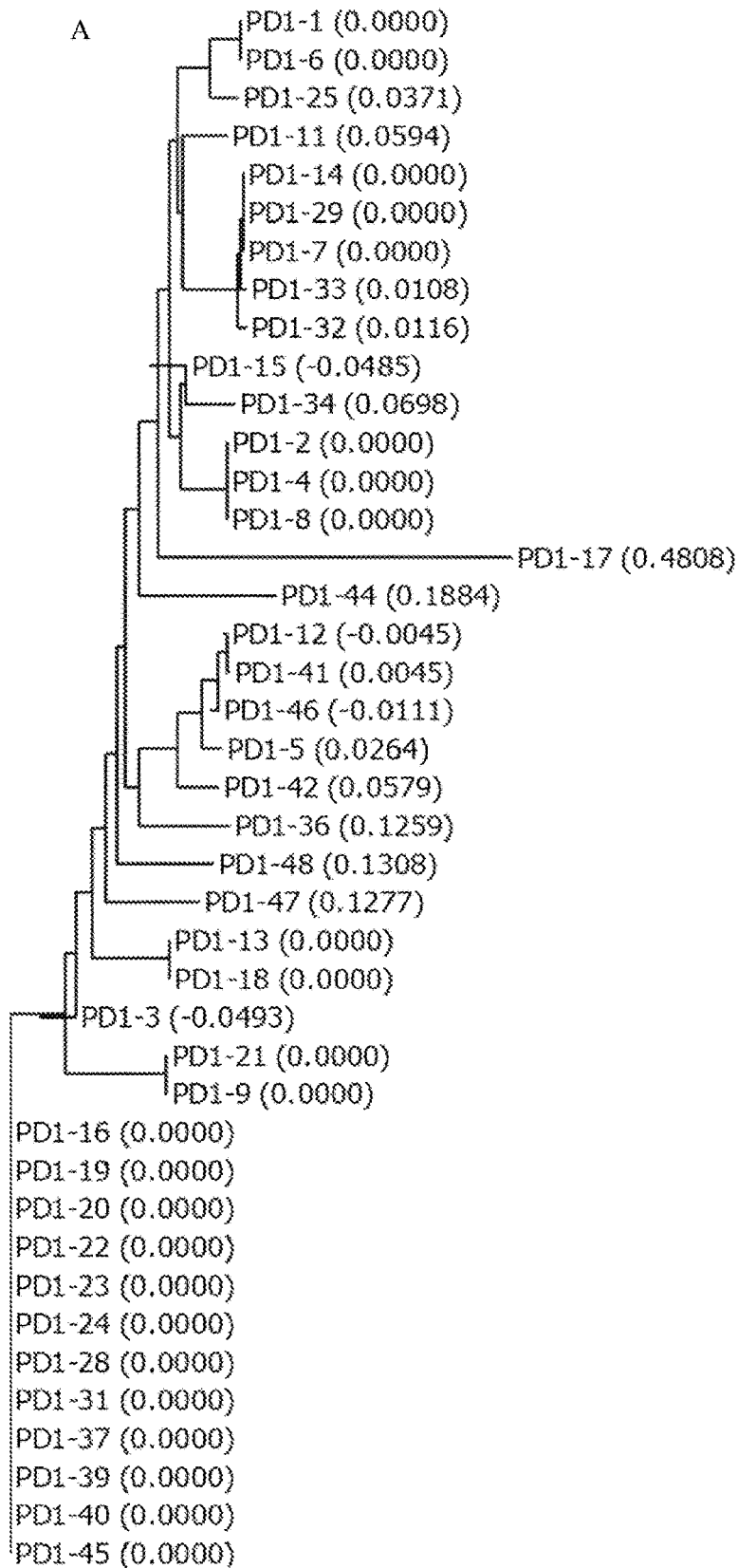
FIG. 3 shows sequence analysis of PD-1-binding nucleic acid aptamers isolated from SELEX screening. Panel A is a tree view showing correlation of the isolated PD-1-binding aptamers. Panel B shows sequence detail of the clustering PD-1 aptamers. The conserved nucleotides, CCATCTCCC (SEQ ID NO: 1), within the PD-1 aptamers are highlighted with boxes. The nucleotide sequences of the aptamers provided in FIG. 3, panel B are as follows: PD1-1 (SEQ ID NO: 16); PD1-2 (SEQ ID NO: 24); PD1-3 (SEQ ID NO: 25); PD1-4 (SEQ ID NO: 24); PD1-5 (SEQ ID NO: 26); PD1-6 (SEQ ID NO: 16); PD1-7 (SEQ ID NO: 10); PD1-8 (SEQ ID NO: 24); PD1-9 (SEQ ID NO: 18); PD1-11 (SEQ ID NO: 27); PD1-12 (SEQ ID NO: 28); PD1-13 (SEQ ID NO: 15); PD1-14 (SEQ ID NO: 10); PD1-15 (SEQ ID NO: 29); PD1-16 (SEQ ID NO: 11); PD1-17 (SEQ ID NO: 31); PD1-18 (SEQ ID NO: 15); PD1-19 (SEQ ID NO: 11); PD1-20 (SEQ ID NO: 11); PD1-21 (SEQ ID NO: 18); PD1-22 (SEQ ID NO: 11); PD1-23 (SEQ ID NO: 11); PD1-24 (SEQ ID NO: 19); PD1-25 (SEQ ID NO: 11); PD1-26 (SEQ ID NO: 32); PD1-28 (SEQ ID NO: 11); PD1-29 (SEQ ID NO: 10); PD1-31 (SEQ ID NO: 11); PD1-32 (SEQ ID NO: 33); PD1-33 (SEQ ID NO: 34); PD1-34 (SEQ ID NO: 35); PD1-36 (SEQ ID NO: 36); PD1-37 (SEQ ID NO: 11); PD1-39 (SEQ ID NO: 11); PD1-40 (SEQ ID NO: 11); PD1-41 (SEQ ID NO: 37); PD1-42 (SEQ ID NO: 38); PD1-44 (SEQ ID NO: 39); PD1-45 (SEQ ID NO: 11); PD1-46 (SEQ ID NO: 40); PD1-47 (SEQ ID NO: 41); PD1-48 (SEQ ID NO: 42).
Figure 3:
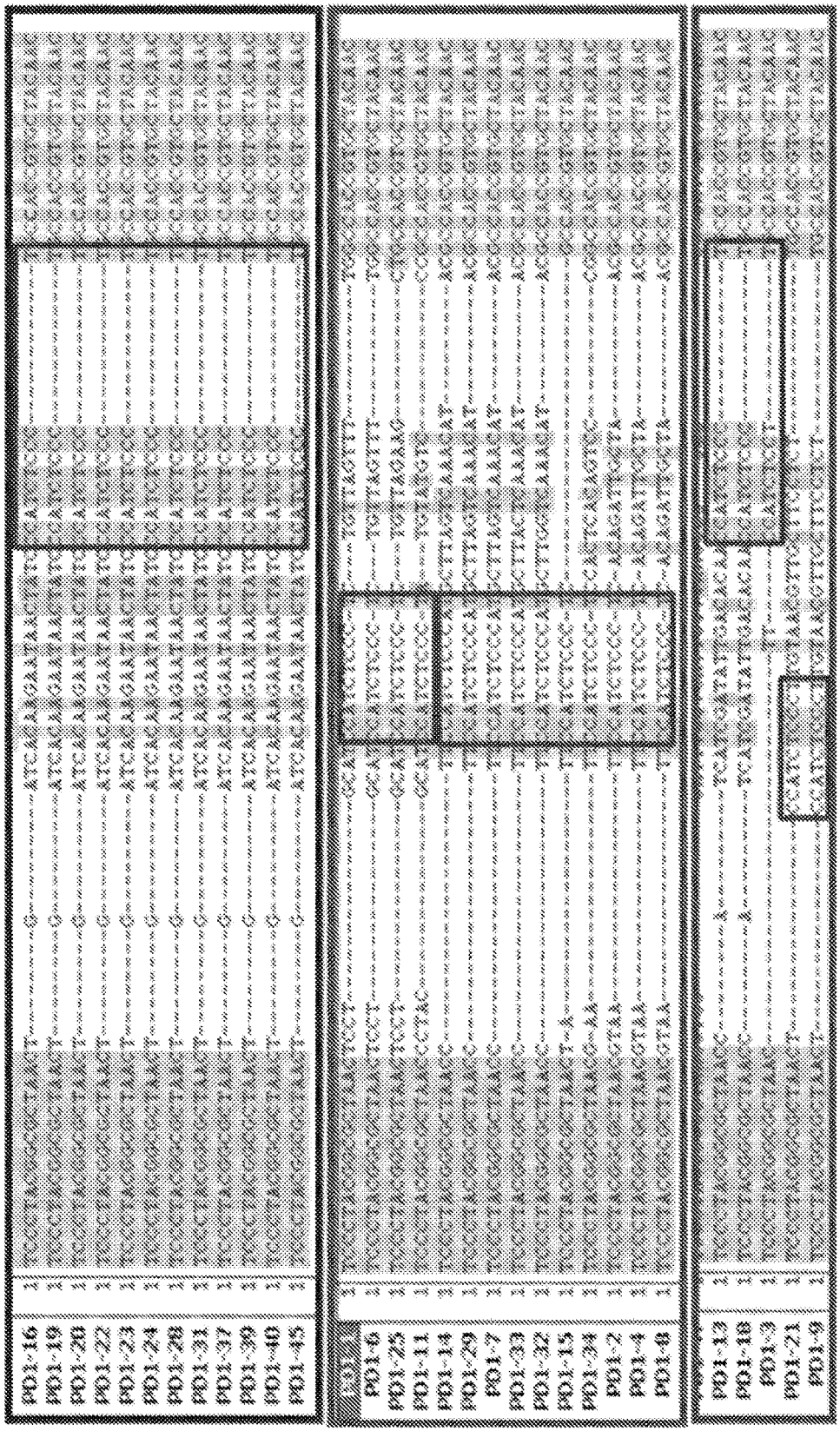

Panel A of FIG. 3 shows the tree view result of PD-1 aptamer. Panel B of FIG. 3 shows the sequence detail of the clustering PD-1 aptamers, which bind to PD-1. The boxed regions indicate the conserve region within the PD-1 aptamer. The aptamer pool from round 16 was TA cloning and 50 clones were selected for sequencing. The sequences were analyzed by clustering software. The tree view result indicates a dominant population was evolved in pool 16 (FIG. 3. Panel A). FIG. 3, panel B shows the detailed sequence information for PD1 aptamers, including a conserved region including 9 nucleotide bases. The 9 nucleotide bases are CCATCTCCC (SEQ ID NO: 1). Nucleic acids comprising this core sequence are expected to bind to PD-1. The nucleic acid sequences of SEQ ID NOs: 24-42 are shown below:

PD1-2

(SEQ ID NO: 24)
TCCCTACGGCGCTAACGTAATTCCATCTCCCTCACAGATTGCTAACGCCA

CCGTGCTACAAC

PD1-3

(SEQ ID NO: 25)
TCCCTACGGCGCTAACTTCCATCTCCTTGCCACCGTGCTACAAC

PD1-5

(SEQ ID NO: 26)
TCCCTACGGCGCTAACTGCCACCGTGCTACAACATCCCTACGGCGCTAAC

TCTCCATCTCCCTTGCCACCGTGCTACAAC

PD1-11

(SEQ ID NO: 27)
TCCCTACGGCGCTAACCCTACGCATCCATCTCCCTATGTATGTCCCGCCA

CCGTGCTACAAC

PD1-12

(SEQ ID NO: 28)
TCCCTACGGCGCTAACATCCATCTCCCTGCCACCGTGCTACAACATCCCT

ACGGCGCTAACTGCCACCGTGCTACAAC

PD1-15

(SEQ ID NO: 29)
TCCCTACGGCGCTAACTATTCCATCTCCCTCGCCACCGTGCTACAAC

PD1-16

(SEQ ID NO: 11)
TCCCTACGGCGCTAACTGATCACAAGAATAACTATCCCATCTCCCTGCCA

CCGTGCTACAAC

PD1-17

(SEQ ID NO: 31)
TCTTTCCGCGGCGGGGGACTGGGATCTTCTTATTGTGAAATCAACCCCG

TAGGA

PD1-26

(SEQ ID NO: 32)
TCCCTACGGCGCTAACTCCTGCATCCATCTCCCTCTGTTAGAAGCTGCCA

CCGTGCTACAAC

PD1-32
(SEQ ID NO: 33)
TCCCTACGGCGCTAACCTTCCATCTCCCATGCTTGGTCAAACATACGCCA

CCGTGCTACAAC

PD1-33
(SEQ ID NO: 34)
TCCCTACGGCGCTAACCTTCCATCTCCCATGCTTACTCAAACATACGCCA

CCGTGCTACAAC

PD1-34
(SEQ ID NO: 35)
TCCCTACGGCGCTAACGAATTCCATCTCCCTCCACTCACAGTCCCGGCCA

CCGTGCTACAAC

PD1-36
(SEQ ID NO: 36)
TTCCTACGGCGCTAACTCCTGTTCCCCTCACAACACCCCTGGGCAGGCCA

CCGTGCTACAAC

PD1-41
(SEQ ID NO: 37)
TCCCTACGGCGCTAACCATCTCCCTGCCACCGTGCTACAAC

PD1-42
(SEQ ID NO: 38)
TCCCTACGGCGCTAACTGTCCTCGCATCCCATCTCCCTACGGCGCTAACT

GCCACCGTGCTACAAC

PD1-44
(SEQ ID NO: 39)
TCCCTACGGCGCTAACGTTGTGATAAGAGGTTACAAGTTTTTCACCGCCA

CCGTGCTACAAC

PD1-46
(SEQ ID NO: 40)
TCCCTACGGCGCTAACTGCCACCGTGCTACAACATCCCTACGGCGCTAAC

CATCTCCCTGCCACCGTGCTACAAC

PD1-47
(SEQ ID NO: 41)
TCCCTACGGCGCTAACCTGGCATTTCCTGATTGTTTAACGCGGCCGGCCA

TCGTGCTACAAC

PD1-48
(SEQ ID NO: 42)
TCCCTACGGCGCTAACAATGGTCCATACTACCGACATCAAGTCCCGCCA

TCGTGCTACAAC

Example 4: Affinity and Structure Analysis of Anti-PD-1 Aptamers PD7 and PD16

Figure 4:
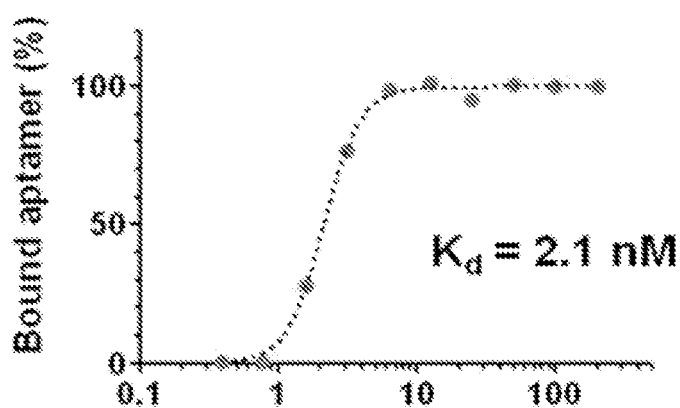
FIG. 4 shows binding activity and predicted structures of two exemplary anti-PD-1 aptamers PD16 and PD7. Panel A is a chart showing the PD-1 binding affinity of PD16 and panel B is a chart showing the PD-1 binding affinity of PD7. The dissociation constant ($K_d$) of PD7 and PD16 is 9.7 nM and 2.1 nM, respectively. Panel C shows the predicted secondary structures of PD-1 aptamers PD16 (SEQ ID NO:11) and PD7 (SEQ ID NO:10) as determined by Mfold. The conserved CCATCTCCC (SEQ ID NO: 1) is highlighted within dotted borders. The $\Delta G$ for the predicted structures of PD7 and PD16 are −1.7 and −0.8, respectively.
Figure 4:
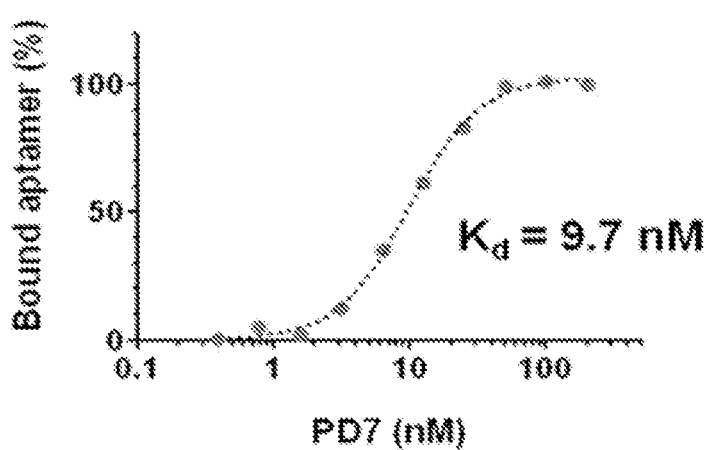
Figure 4:
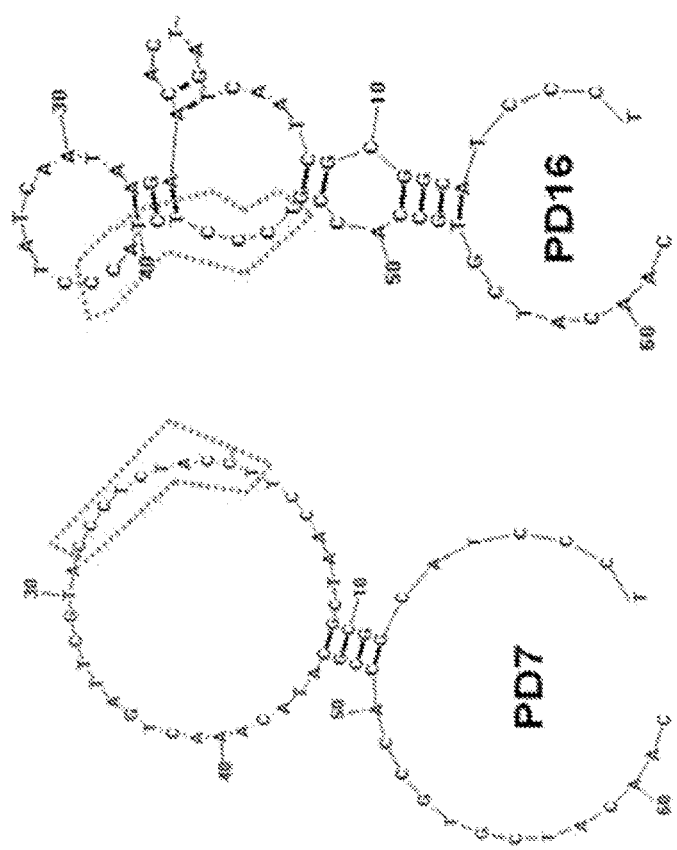

PD7 and PD16 were selected for presenting the two major sequence populations within PD-1 aptamer pools. The total binding assays indicate the binding affinity of PD7 (FIG. 4, panel B) and PD16 (FIG. 4, panel A) is 9.7 nM and 2.1 nM, respectively. Using Mfold software to predict the secondary structure of PD7 and PD16 aptamer, the result indicates that there is no significant similarity between the secondary structures of PD7 and PD16 (Figure, panel C). Moreover the conserved region in PD7 and PD16 is located in different part and involved in stem/loop structure (FIG. 4, panel C). This result suggests that the secondary structure might not be the major factor that responsible for its binding to PD-1 protein.

Example 5: Identification of PD-1 Antagonistic Aptamers

Figure 5:
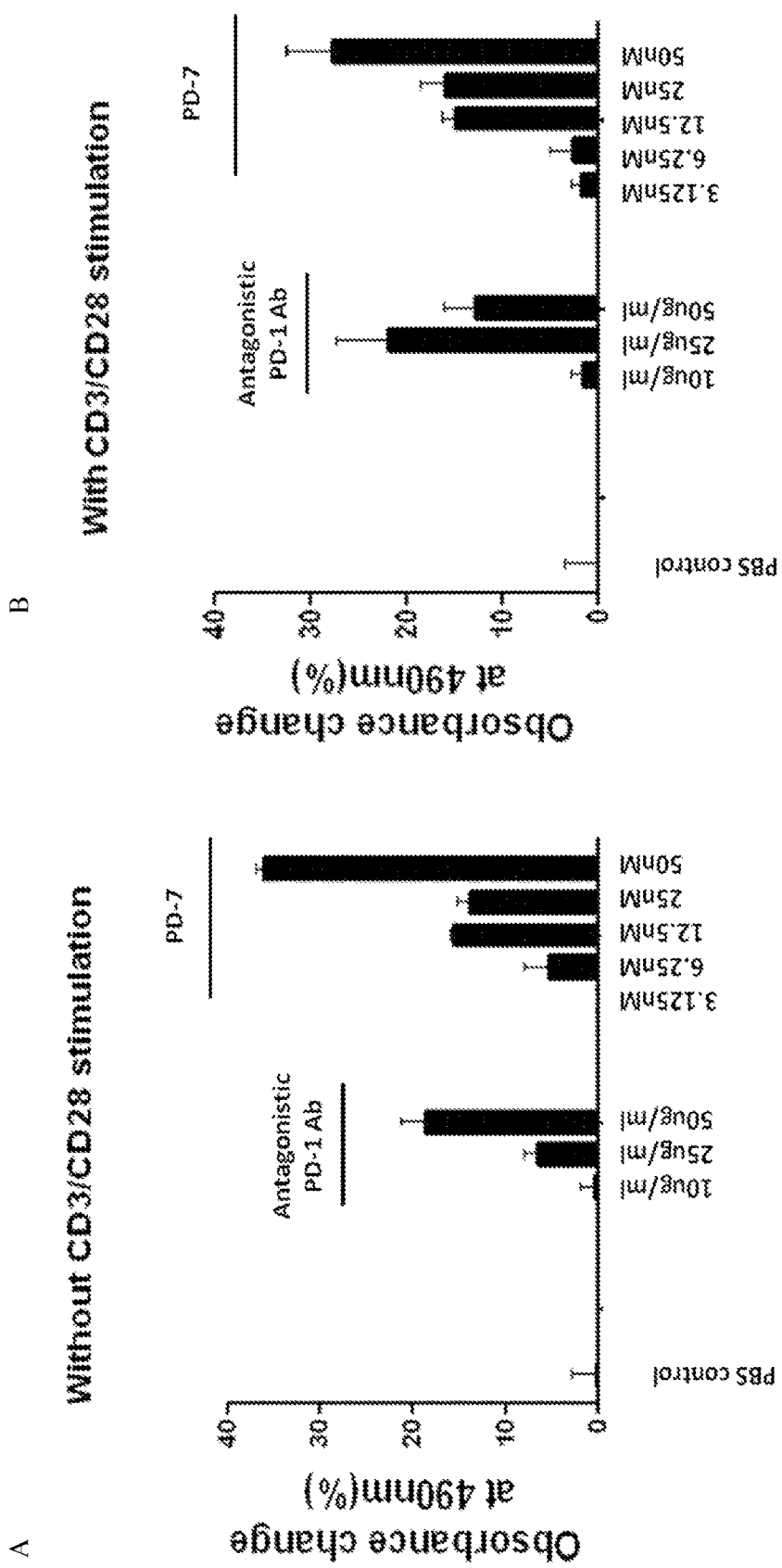
FIG. 5 includes charts showing that an exemplary anti-PD-1 aptamer, PD7, promoted T cell proliferation. The PD7 aptamer treatment promoted T cell proliferation and the effect is more significant than treatment of PD-1 antagonistic antibody. Panel A is a chart showing experimental results from experiments performed without CD3/CD28 stimulation. Panel B is a chart showing experimental results from experiments performed with CD3/CD28 stimulation.

Seven of the PD-1 apatmers were selected for T cell proliferation assays to present seven major groups of sequences. The seven PD-1 aptamers tested in this study were PD16, PD13, PD6, PD7, PD8, PD9, and PD24, the nucleotide sequences of which are shown below. All these aptamers increased T cell proliferation as compared to the control group. One of the aptamers, PD7, showed the strongest effect in induction of T cell proliferation and is a stronger T cell activator then a PD-1 antagonistic antibody in the absence (FIG. 5, panel A) or presence (FIG. 5, panel B) of CD3/CD28 stimulation. The result indicates an increase of over 30% of the signal with PD7 as compared to the PD-1 antagonistic antibody (FIG. 5, panel A).

PD16:
(SEQ ID NO: 11)
TCCCTACGGCGCTAACTGATCACAAGAATAACTATCCCATCTCCCTGCCA

CCGTG CTACAAC

PD13:
(SEQ ID NO: 15)
TCCCTACGGCGCTAACCATCATCGATATTGACACAACCATCTCCCTGCCA

CCGTGCTACAAC

PD6:
(SEQ ID NO: 16)
TCCCTACGGCGCTAACTCCTGCATCCATCTCCCTCTGTTAGTTTTGGCCA

CCGTGCTACAAC

PD7:
(SEQ ID NO: 10)
TCCCTACGGCGCTAACCTTCCATCTCCCATGCTTAGTCAAACATACGCCA

CCGTGCTACAAC

PD8:
(SEQ ID NO: 17)
TCCCTACGGCGCTAACGTAATTCCATCTCCCTCACAGATTGCTAACGCCA

CCGTGCTACAAC

PD9:
(SEQ ID NO: 18)
TCCCTACGGCGCTAACTCCATCTCCCTTGTAACGTTGCTTCCTCTTGCCA

CCGTGCTACAAC

PD24:
(SEQ ID NO: 19)
TCCCTACGGCGCTAACCGTCATCGTTAATATATTGTCCTCGCATAAGCCA

CCGTGCTACAAC

Example 6: Antagonist Activity of Anti-PD-1 Aptamer Sequences

Additional aptamer nucleotide sequences of anti-PD-1 aptamers isolated via SELEX, as described in Example 1, were identified based on statistical analysis using next-generation sequencing (NGS) data:

```
Core 1 -
CCATCTCCC;              (SEQ ID NO: 1)

Optimized Core 1 -
CCATCTCCCGTCC           (SEQ ID NO: 7)
```

-continued

```
Core 2 -
TATATTGTCC;          (SEQ ID NO: 20)

Core 3 -
GTACAGTT;            (SEQ ID NO: 21)

Core 4 -
GCACTACA;            (SEQ ID NO: 4)

Core 5 -
GTACATCA;            (SEQ ID NO: 22)
and

Core 6 -
GCTACTGT.            (SEQ ID NO: 23)
```

Figure 6:
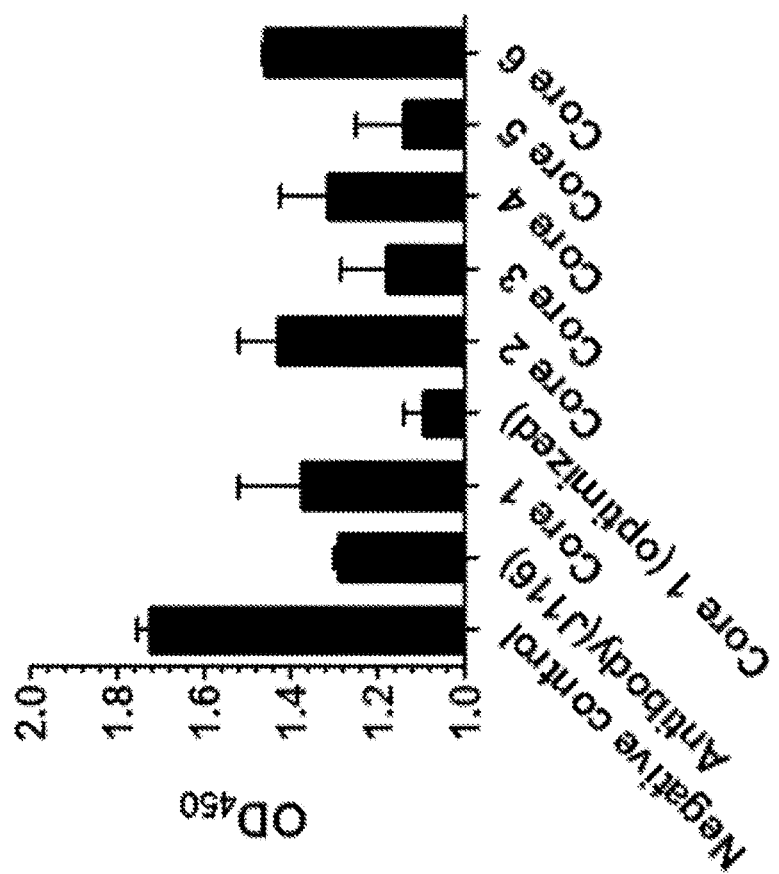
FIG. 6 is a graph showing the results of a PDL1 competition assay using the aptamer core nucleotide sequences of Core 1, Core 1 (optimized), Core 2, Core 3, Core 4, Core 5 and Core6.
Figure 7:
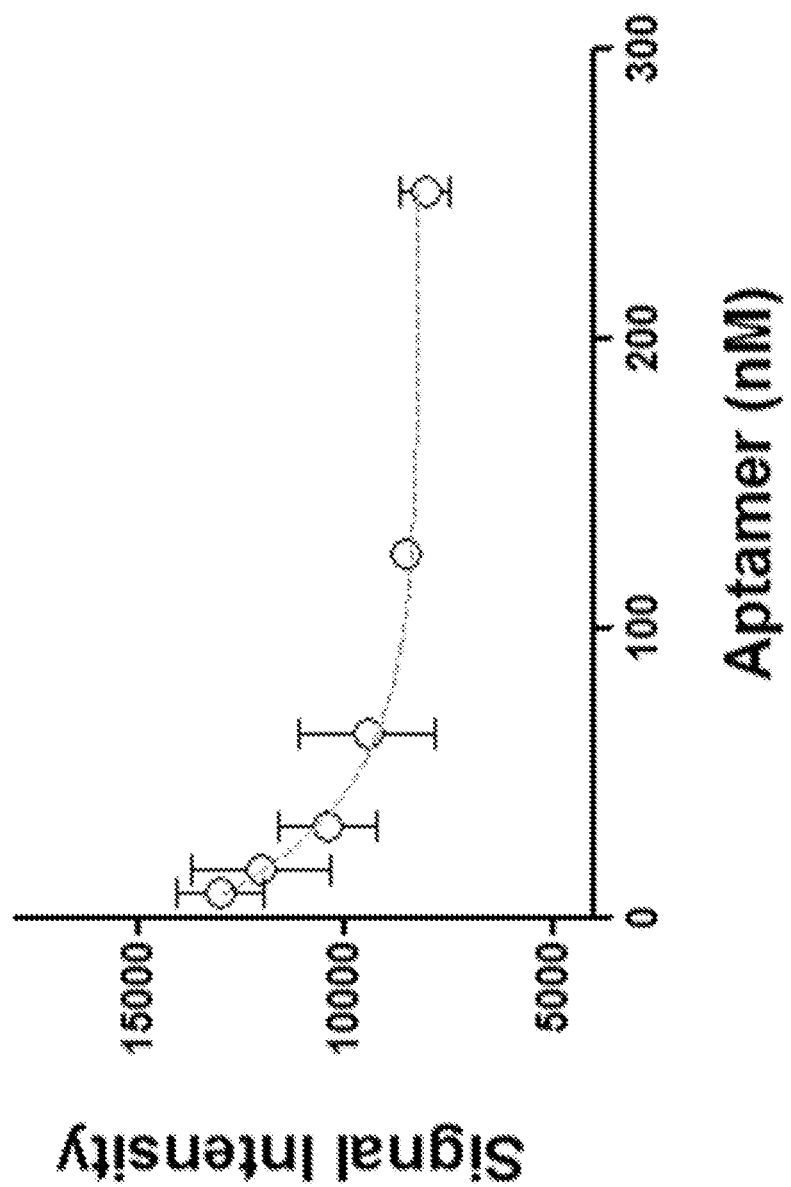
FIG. 7 is a graph showing the dose-dependent inhibition of the interaction between PDL1 and PD1 using Core 1 in a PDL1 competition assay. The IC50 of Core 1 is 31.18 nM, which represents the amount of Core 1 nucleic acid required to inhibit 50% of the PDL1/PD1 interaction.
Figure 8:
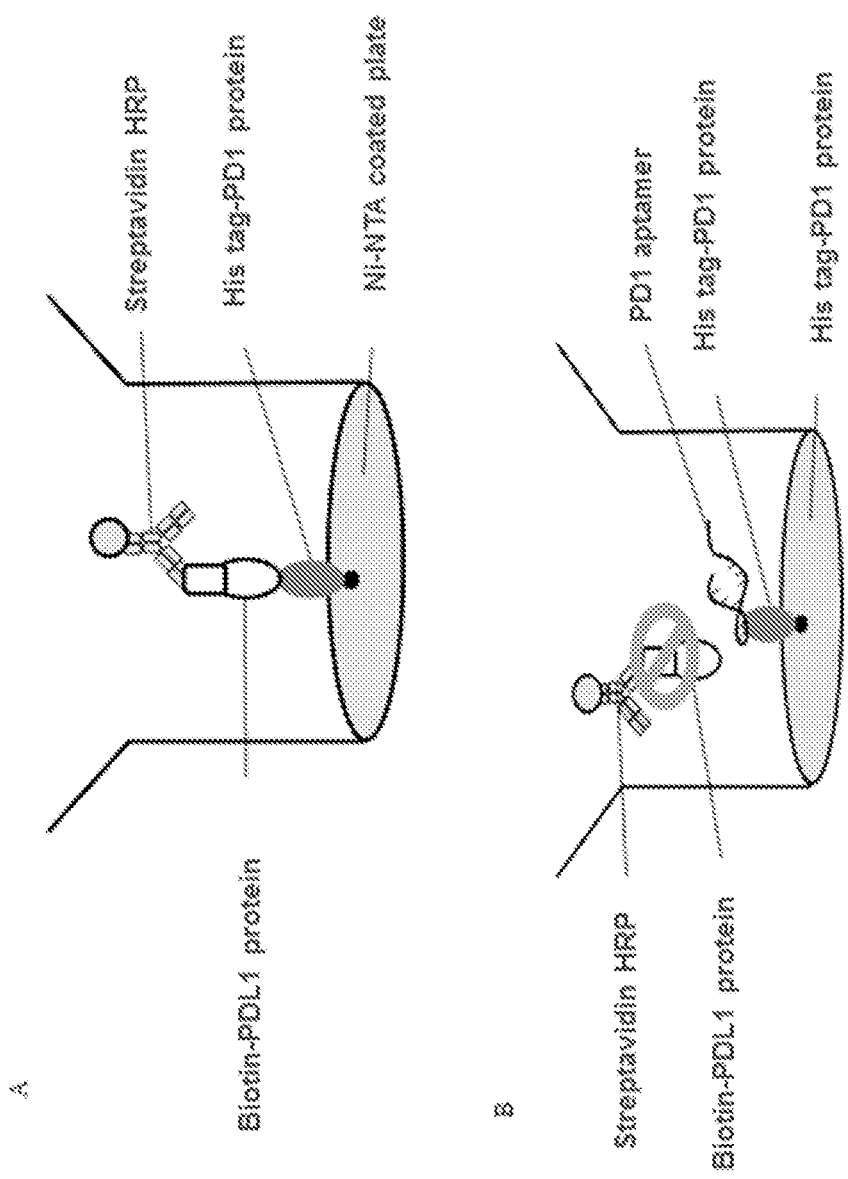
FIG. 8 shows schematic representations of the PDL1 competition assay. Panel A shows a histidine tagged PD1 protein (His tag-PD1 protein) immobilized on a nickel nitrilotriacetic acid (Ni-NTA) coated plate. The histidine tagged PD1 protein binds Biotin-tagged PDL1 (Biotin-PDL1) in the absence of a PD1 antagonistic aptamer, which can be detected by Streptavidin conjugated to horseradish peroxidase (HRP). Panel B shows that in the presence of an antagonistic PD1 aptamer, the interaction between PD1 and PDL1 is out-competed and the HRP does not bind to produce a signal (e.g., a chemiluminescent signal upon addition of ECL).

Each of the above aptamer nucleotide sequences were tested for PD-1 antagonistic activity using an in vitro competition assay. Briefly, 200 ng of histidine-tag labeled PD-1 receptors (His tag-PD1 protein) were coated on nickel-nitrilotriacetic acid (Ni-NTA) coated plates and treated with Fc-labeled PDL-1 protein/aptamer mixture. Protein G-HRP and ECL substrate was used to determine the binding signal. The PD-1 antagonistic antibody J116 was used as a positive control and the negative control was performed in the absence of aptamer or antibody. A schematic representation of the competition assay is shown in FIG. 8, panels A and B. Each of the aptamer sequences (Cores 1-6 and Core 1(optimized)) were tested in the in vitro competition assay at a concentration of 200 nM. In the competition assay, each aptamer nucleotide sequence inhibited the interaction between PD-1 and PDL-1 as shown in FIG. 6. Further, the IC50 for antagonizing PD-1/PDL-1 binding for Core 1, CCATCTCCC (SEQ ID NO: 1), was determined to be 31.18 nM using the in vitro competition assay (FIG. 7). These data indicate that aptamer nucleotide sequences can antagonize PD-1 binding to PDL-1.

Example 7: Anti-PD-1 Aptamers Cross-React with PD-1 of Different Species

Figure 9:
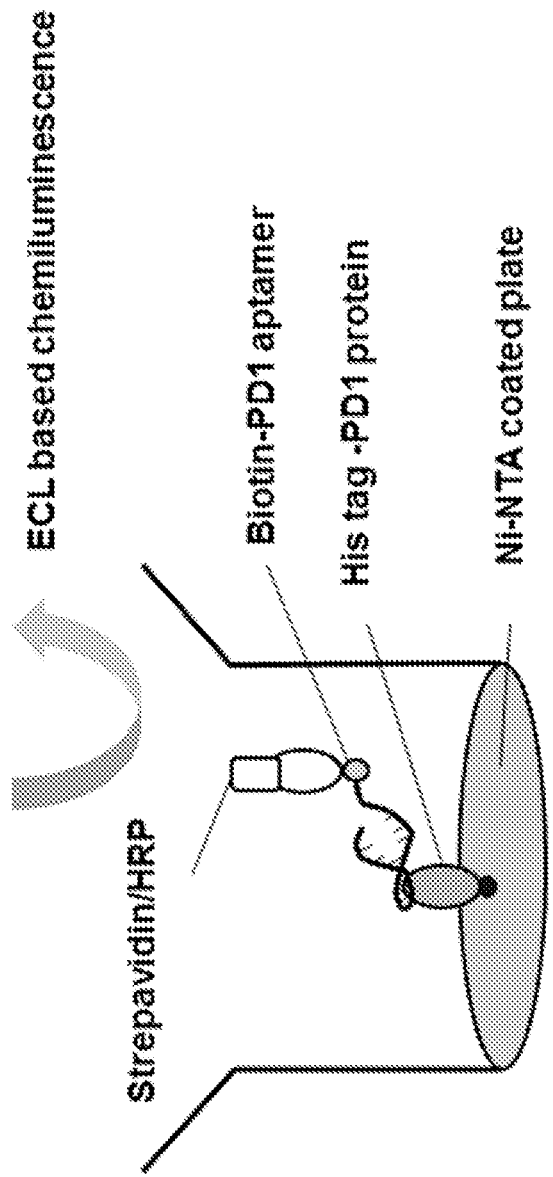
FIG. 9 is a schematic representation of a PD1 aptamer binding assay. A histidine tagged PD1 protein (His tag-PD1 protein) is immobilized on a nickel nitrilotriacetic acid (Ni-NTA) coated plate. Binding of an antagonistic PD1 aptamer conjugated to biotin (Biotin-BD1 aptamer) to the immobilized PD1 can be detected using streptavidin-conjugated horseradish peroxidase (Streptavidin/HRP). The bound HRP can be detected upon addition of a substrate that luminesces when it contacts HRP (e.g., ECL).

Aptamers were used to demonstrate cross reactivity of PD-1 binding with other species using an in vitro PD-1 aptamer binding assay. Briefly, 200 ng of histidine-tag labeled PD-1 receptors (His tag-PD1 protein) were coated on nickel-nitrilotriacetic acid (Ni-NTA) coated plates and treated with aptamers conjugated at their 5' end to biotin (Biotin-PD-1 aptamer). Binding of the aptamers to PD-1 was detected using streptavidin-HRP and ECL substrate. A schematic representation of the in vitro PD-1 binding assay is shown in FIG. 9. The aptamers tested were:

```
PD7 -
        (SEQ ID NO: 10; core sequence in boldface)
TCCCTACGGCGCTAACCTTCCATCTCCCATGCTTAGTCAAACATACGC

CACCGTGCTACAAC;

PD100 -
        (SEQ ID NO: 12; core sequence in boldface)
TCCCTACGGCGCTAACCCTCCCCTAGTATATATTGTCCTCGTCTATG

CCACCGTGCTACAAC.
```

```
                         (SEQ ID NO: 1)
Core 1 -
CCATCTCCC;
and (SEQ ID NO: 20)
Core 2 -
TATATTGTCC.
```

The above aptamers were tested for binding to human, mouse, rat, rhesus monkey and/or canine PD-1 using the in vitro PD-1 binding assay depicted in FIG. 9. The dissociation constant for binding of the aptamers to PD-1 (from each species) was determined and is shown in Table 1. These data indicate that these aptamers can bind PD-1 in a wide variety of species including humans, mice, rats, monkeys and dogs.

TABLE 1

Binding affinity of aptamers PD7, PD100, Core1 and Core 2 to PD-1 of different species (human, mouse, rat, rhesus monkey and canine).

|  | PD7(Inclu. Core1) | PD100(Inclu. Core2) | Core1 | Core2 |
|---|---|---|---|---|
| HUMAN | +++ | +++ | +++ | +++ |
| MOUSE | +++ | ++ | ++ | +++ |
| RAT | +++ | +++ | ND | ND |
| RHESUS | +++ | ++ | ND | ND |
| CANINE | ++ | +++ | ++ | ++ |

Kd values:
+++: below 20 nM
++: 20 nM~100 nM
ND: non determined

Figure 10:
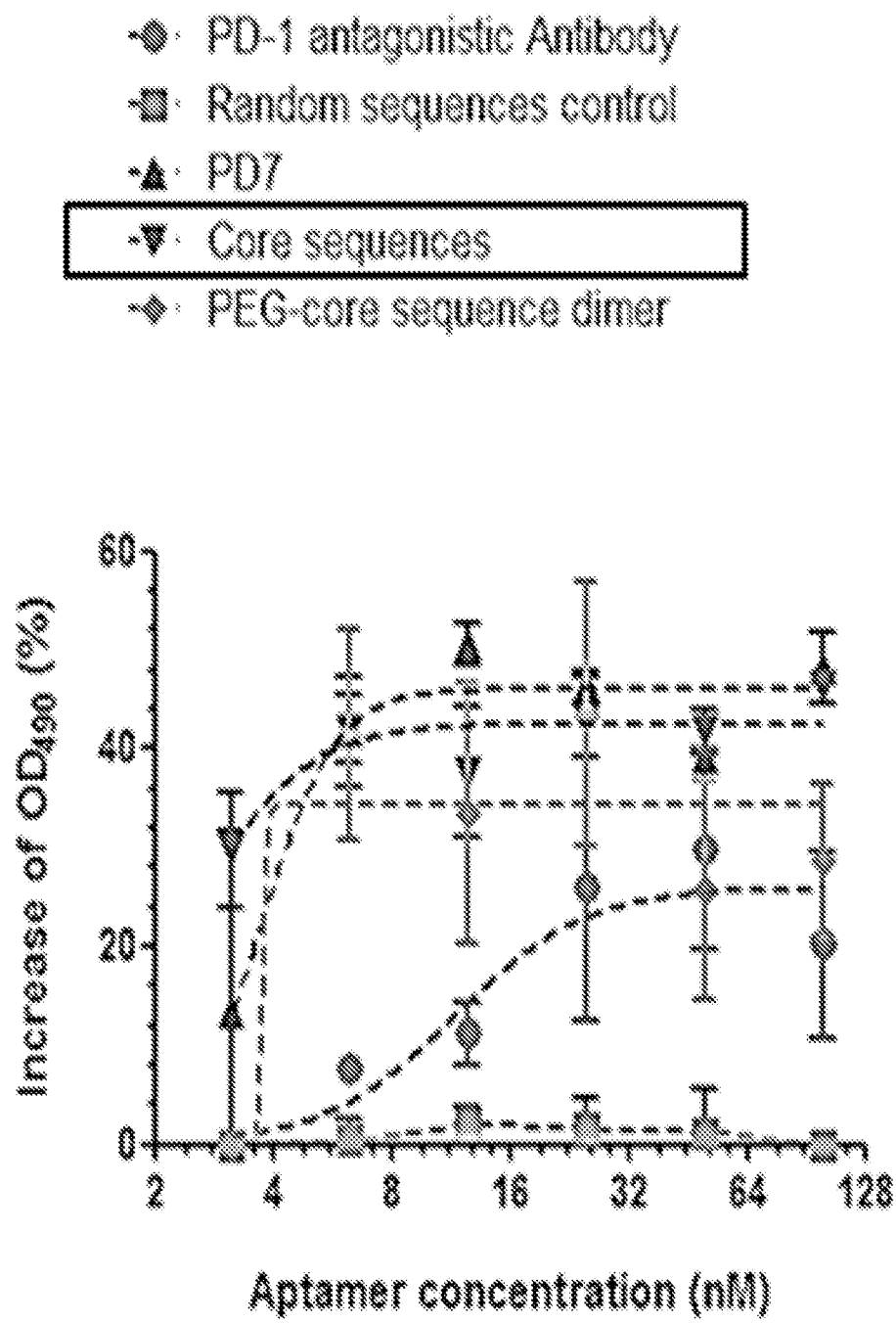
FIG. 10 is a graph showing lymphocyte proliferation activity in the presence of (i) a PD-1 antagonistic antibody, (ii) random control sequences, (iii) the PD7 aptamer (SEQ ID NO: 10), (iv) core sequence (SEQ ID NO: 13) which comprise the core nucleic acid sequence set forth in SEQ ID NO: 1, and (v) the peglyated PD7 dimer (Core sequences), shown in FIG. 11.
Figure 11:
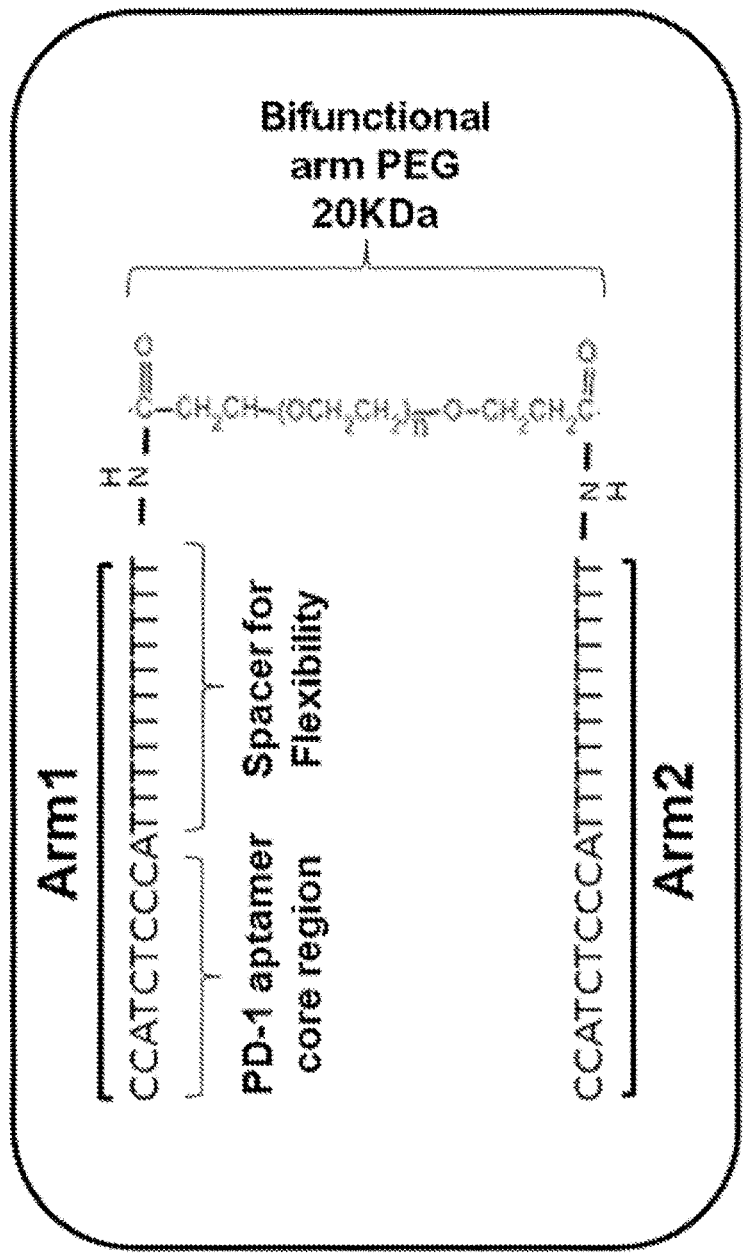
FIG. 11 is a schematic of a non-limiting example of a dimeric aptamer molecule. The schematic shows a linear 20 kDa PEG molecule conjugated with two separate aptamer sequences, CCATCTCCCATTTTTTTTTT (SEQ ID NO: 14) comprising the core nucleic acid sequence of SEQ ID NO: 1 and a PolyT linker, at each end of the PEG molecule.

Example 8: Anti-PD-1 Aptamers Induced Lymphocyte Proliferation and CD8+ T-Cell Proliferation A lymphocyte proliferation assay was used to demonstrate the ability of anti-PD-1 aptamers, including both free aptamers and PEG-conjugated aptamers (PEG conjugates), to promote lymphocyte proliferation. Briefly, human peripheral blood mononuclear cells (PBMCs) were isolated by Ficoll-paque and cultured in complete RPMI medium overnight to stabilize the cells. Stabilized PBMCs were treated with different concentrations of PD-1 aptamer, pegylated aptamer, antagonistic PD-1 antibody, or random control sequences for 48 hours. The total cell number was evaluated using a CellTiter® proliferation kit from the Promega company. The aptamers tested were PD7 (SEQ ID NO: 10), CCATCTCCCA (SEQ ID NO: 13; Core sequence), and peglyated PD7 dimer (shown in FIG. 11):

Each of the above aptamers increased lymphocyte proliferation to a greater degree than the PD-1 antagonistic antibody (FIG. 10). These data indicate that the aptamers, and PEG-core sequence dimers can be used to enhance immune activity.

Further, flow cytometry was used to demonstrate the ability of anti-PD-1 aptamers to promote CD4+ and CD8+ T-cell proliferation, using PD7 and Core 1 as examples. Briefly, mouse CD4+ and CD8+ T-cells were isolated from mouse spleens using magnetic beads. The cells were stained with the fluorescence indication dye, carboxyfluorescein succinimidyl ester (CFSE). The CFSE stained cells were co-cultured with antigen presenting cells (APCs; monocytes and macrophages isolated form mouse PBMCs) and treated with 40 nM of PD7 or 40 nM of the aptamer nucleotide sequence CCATCTCCC (SEQ ID NO: 1) for 72 hours.

Figure 12:
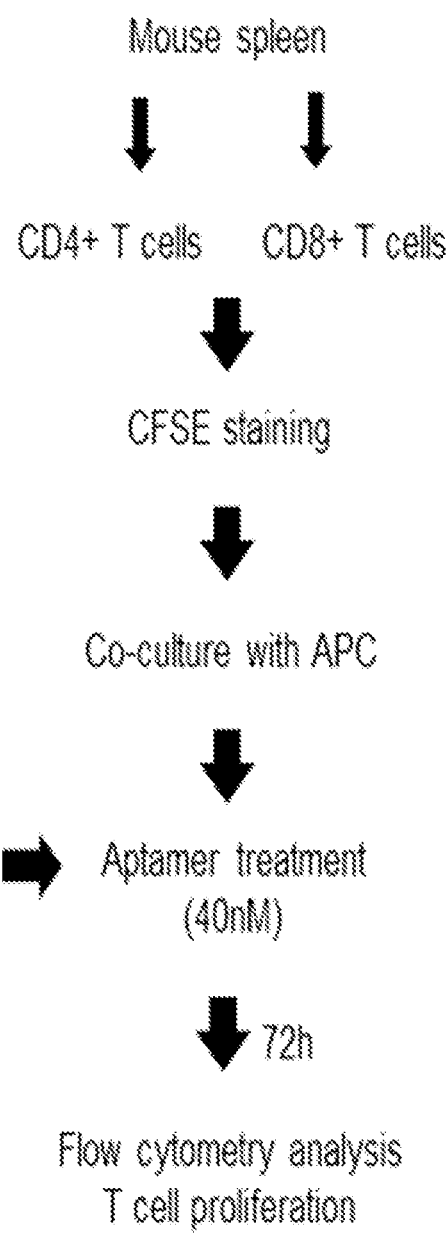
FIG. 12 is a schematic representation of an exemplary $CD4^+$ and $CD8^+$ T-cell proliferation assay.
Figure 13:
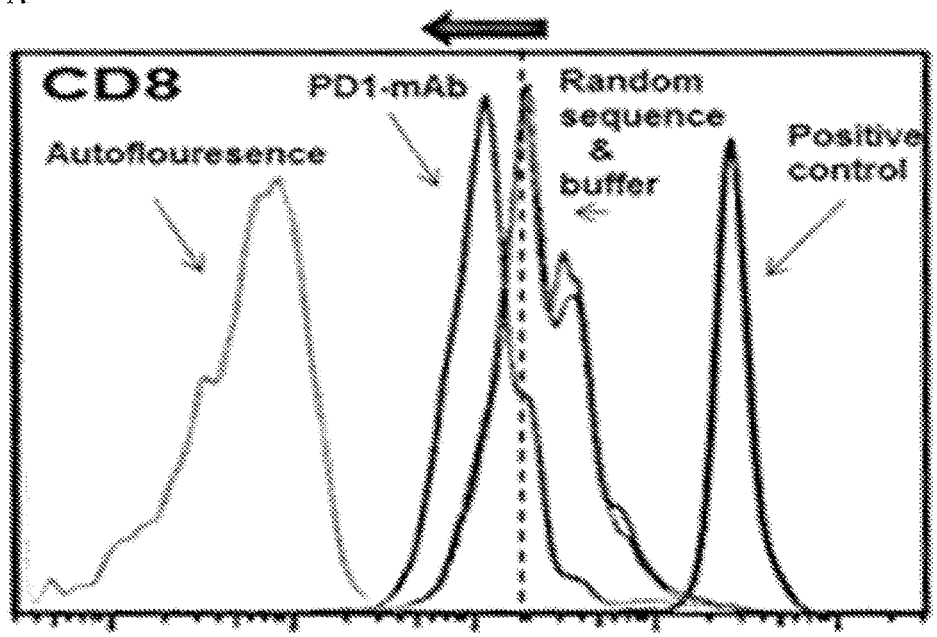
FIG. 13 includes graphs showing the activity of exemplary aptamers PD7 and Core 1 sequence on CD4+ (Panel D) and CD8+ (Panel C) T-cell proliferation and the activity of an antagonistic PD-1 antibody and a random sequence negative control on CD4+ (Panel B) and CD8+ (Panel A) T-cell proliferation.
Figure 13:
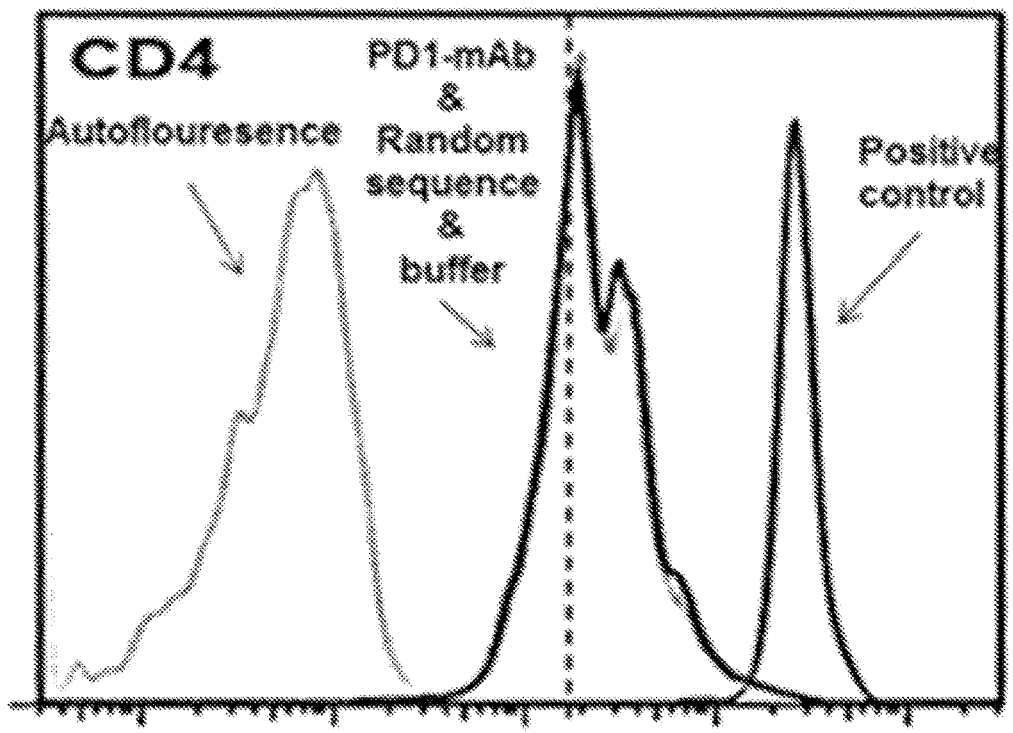
Figure 13:
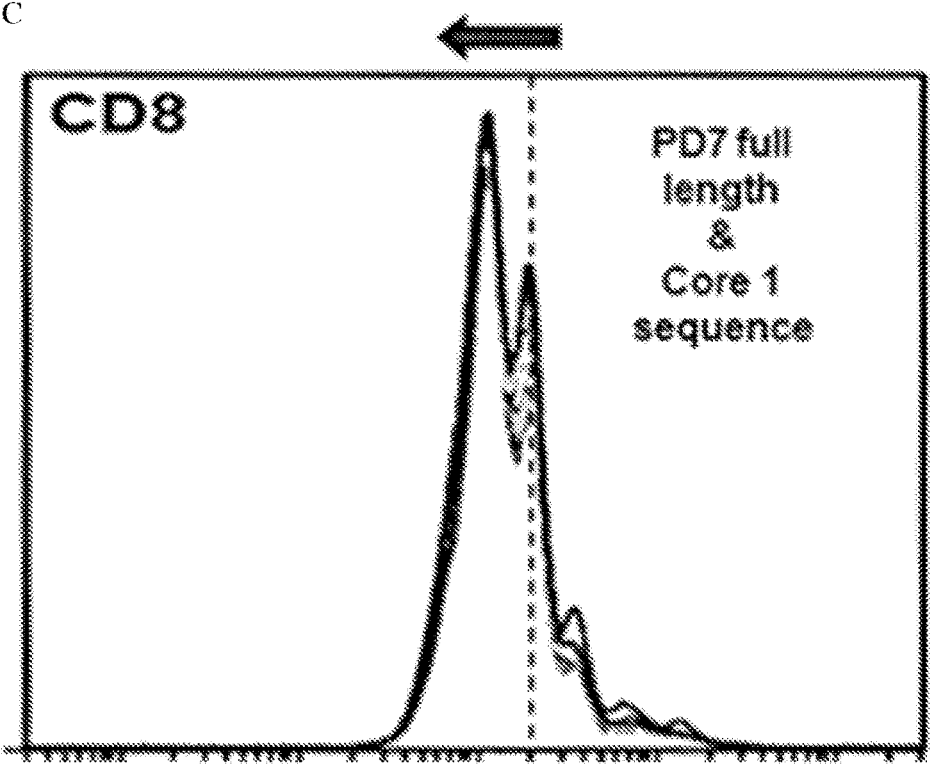
Figure 13:
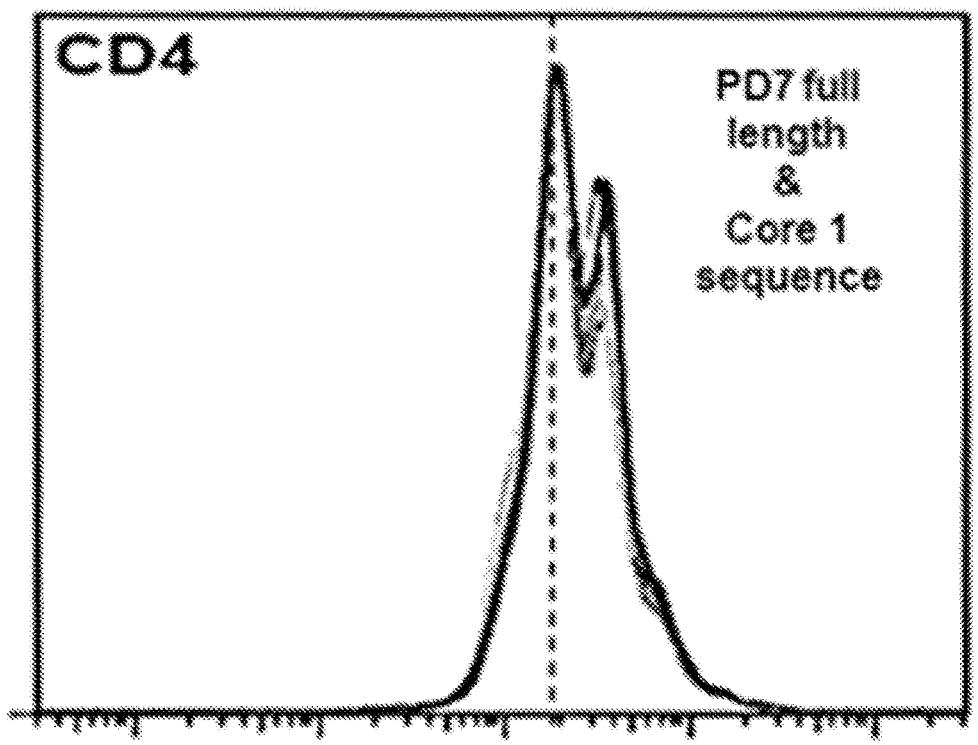

Treatment with an antagonistic PD-1 antibody was used as a positive control and treatment with random DNA sequences was used as a negative control. Flow cytometry was used to monitor the fluorescent intensity of the cell population, where weaker fluorescence signals indicated increased proliferation. A schematic representation of the assay is shown in FIG. 12. Results indicated that the antagonistic PD-1 antibody, the PD7 aptamer and increased $CD8^+$ T-cell proliferation but not $CD4^+$ T-cell proliferation (FIG. 13, panels A-D), while the negative control had no effect on cell proliferation in either cell type (FIG. 13, panels A and B). These data indicate that aptamers comprising the core sequences shown herein can be used to enhance immune activity by promoting $CD8^+$ T-cell proliferation.

Figure 14:
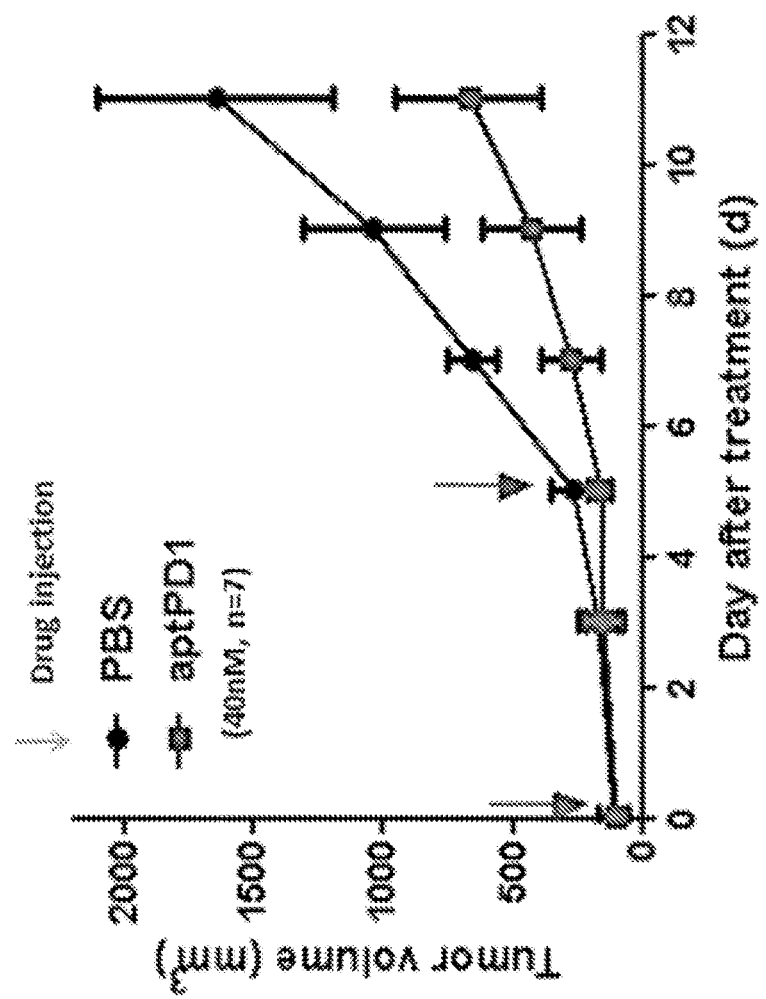
FIG. 14 is a graph showing the tumor growth inhibitory activity of an exemplary aptamer (PD7) in a syngeneic lung cancer mouse model.

Example 9: Anti-PD-1 Aptamer Inhibited Tumor Growth in an In Vivo Syngeneic Mouse Model A syngeneic lung cancer mouse model was used to demonstrate the inhibitory activity of the anti-PD-1 aptamers described herein, on the growth of lung cancer in vivo, using the PD-1 antagonistic aptamer PD7 (SEQ ID NO: 10) as an example. Briefly, mouse Lewis lung cancer cells (ATCC, CRL1642) were subcutaneously transplanted into C57BL/6J mice at day 0 ($2 \times 10^5$ Lewis lung cells per mouse). After tumors reached 100 $mm^3$, mice were separated into the control, PBS treated, group (n=7) or the PD-1 aptamer treated group (n=7). The PD-1 aptamer treated mice were administered 40 nmol of PD7 in PBS and the control mice were administered PBS by intraperitoneal injection. As shown in FIG. 14, the Lewis lung cell syngeneic mice were injected with the PD-1 aptamer on days 0, and 5 (FIG. 14; arrows indicate injection times). Tumor size was measured on days 0, 3, 5, 7, 9 and 11. The tumor size in the PD7 treated mice was reduced by approximately 50% as compared to the tumor size of mice treated with control PBS (FIG. 14) at day 11 post tumor cell injection. These data indicate that the PD7 aptamer can be used to treat lung cancer.

Figure 15:
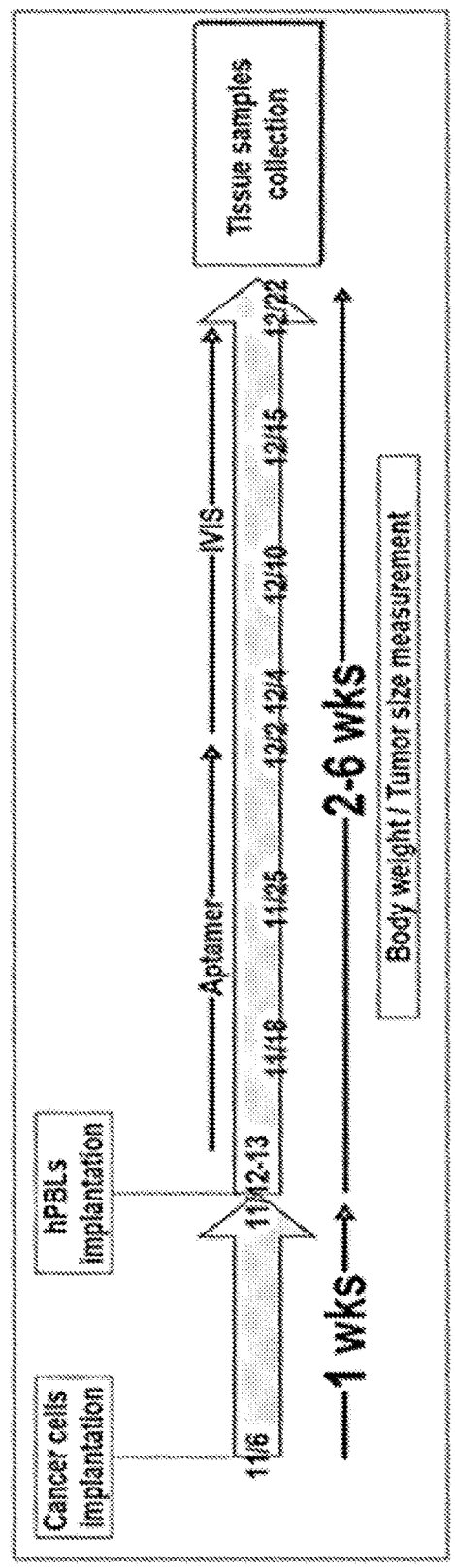
FIG. 15 is a schematic representation of the treatment schedule of a humanized lung cancer mouse model treated with an exemplary aptamer (PD7).
Figure 16:
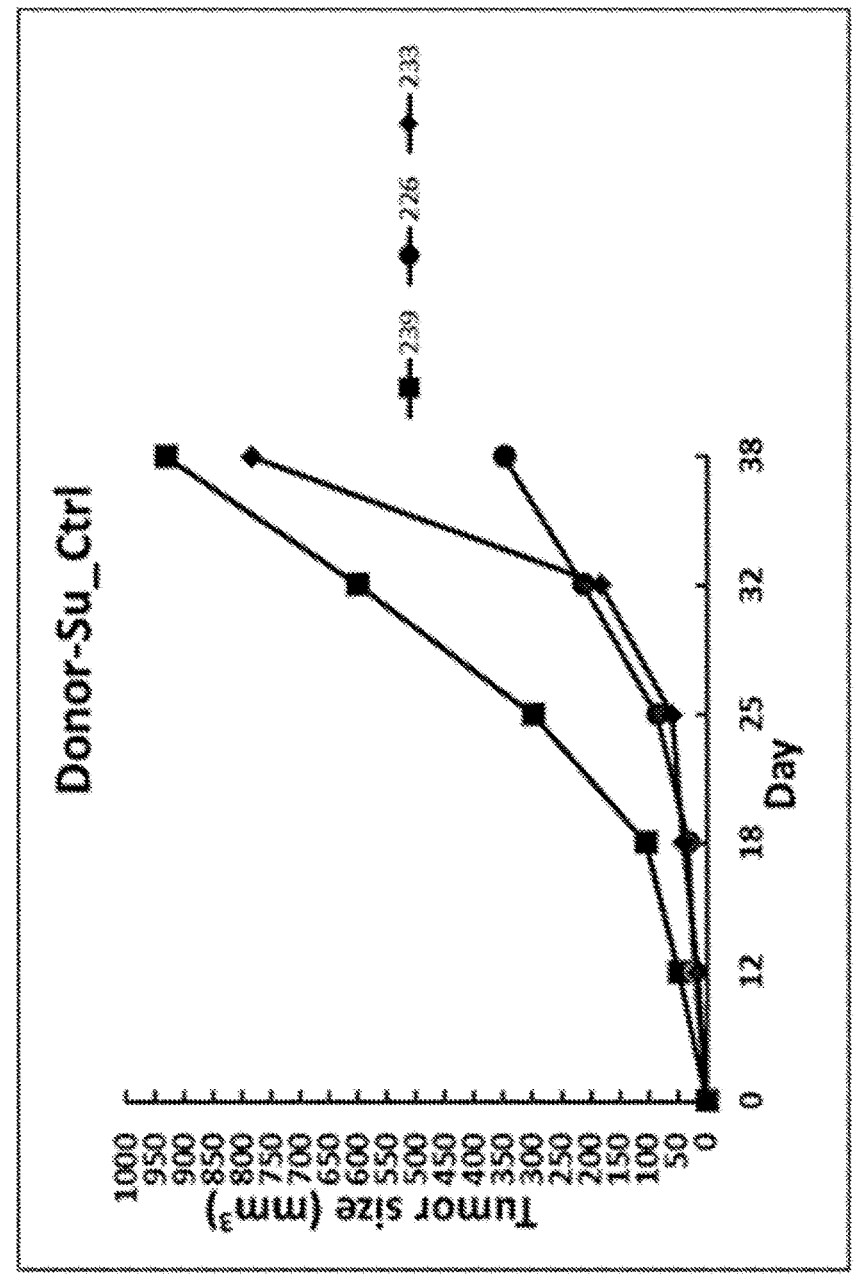
FIG. 16 shows the results of the humanized lung cancer mouse model used to demonstrate the inhibitory activity of the PD-1 antagonistic aptamer PD7 on the growth of lung cancer in vivo. Panel A is a graph showing tumor growth over time in control mice 239, 226 and 233, which are pictured in panels B-D on days 25, 32 and 38, respectively. Panel E is a graph showing tumor growth over time in PD7 treated mice 240, 234 and 235, which are pictured in panels F-H on days 25, 32 and 38, respectively.
Figure 16:
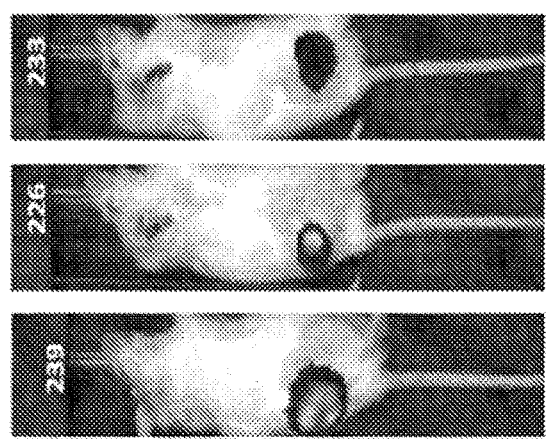
Figure 16:
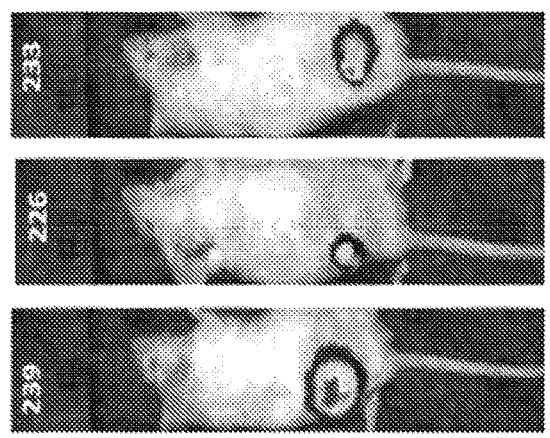
Figure 16:
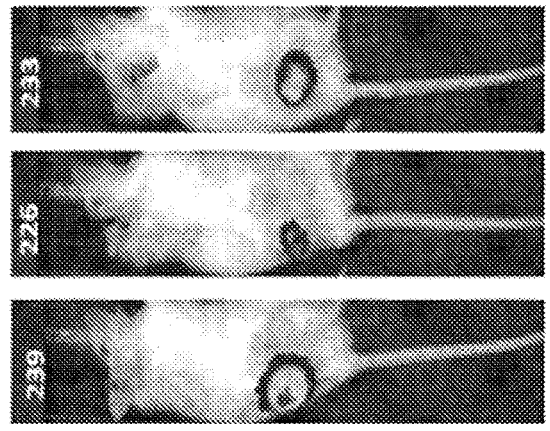
Figure 16:
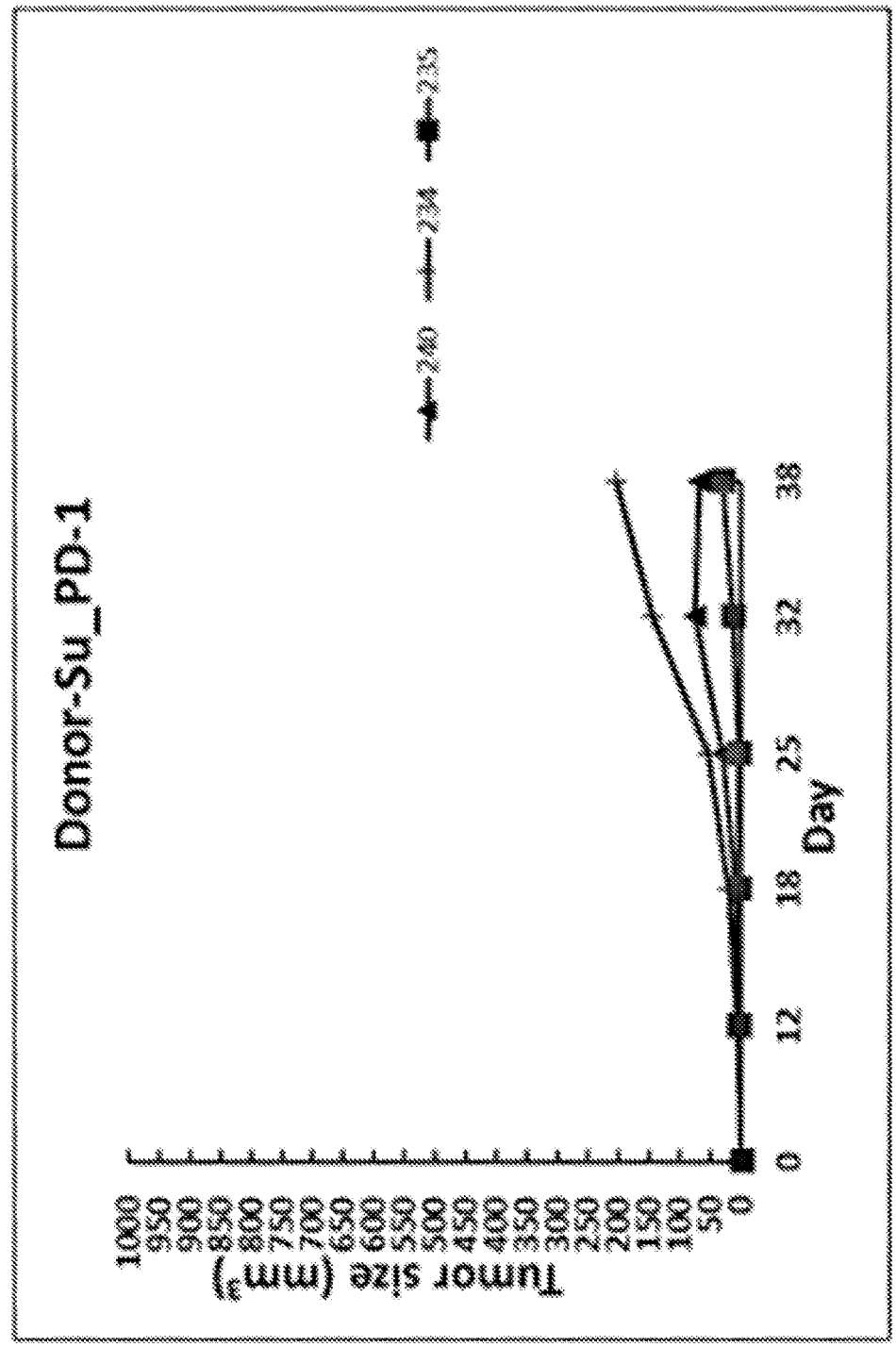
Figure 16:
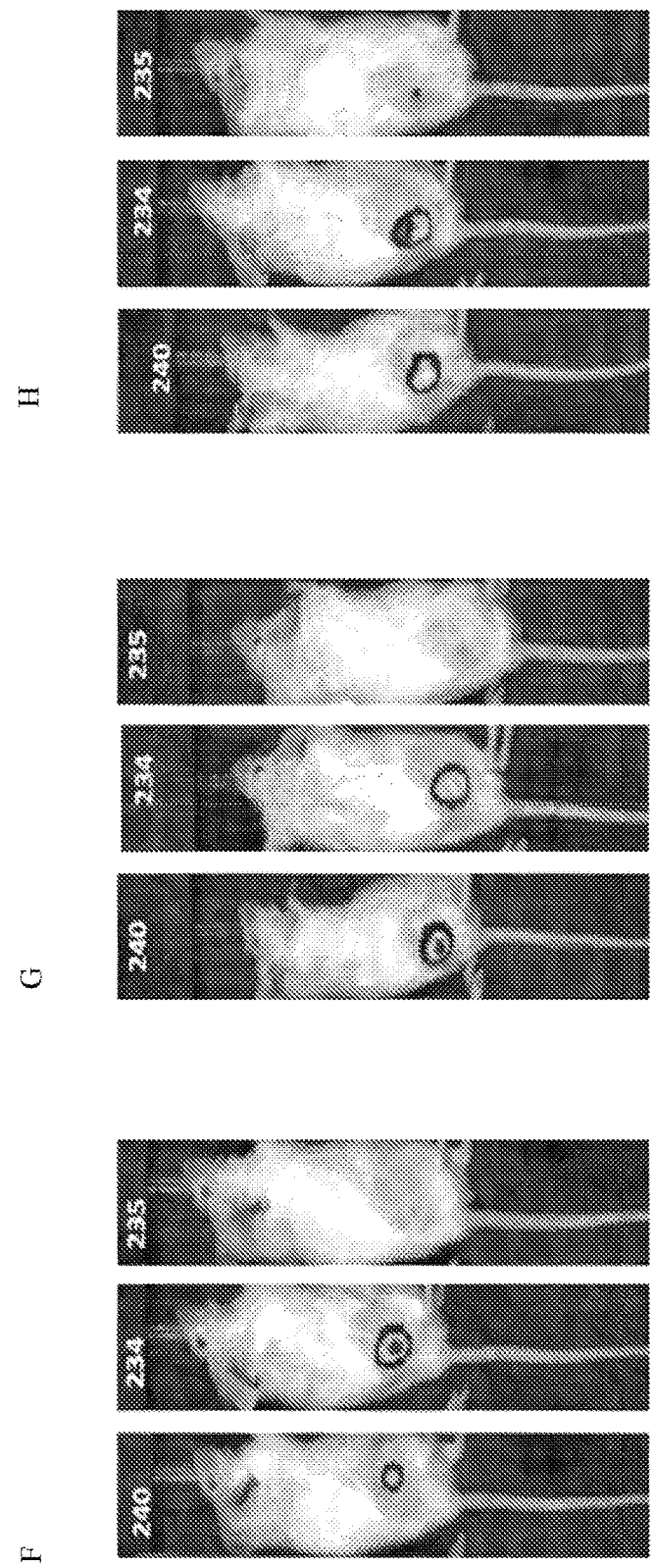
Figure 17:
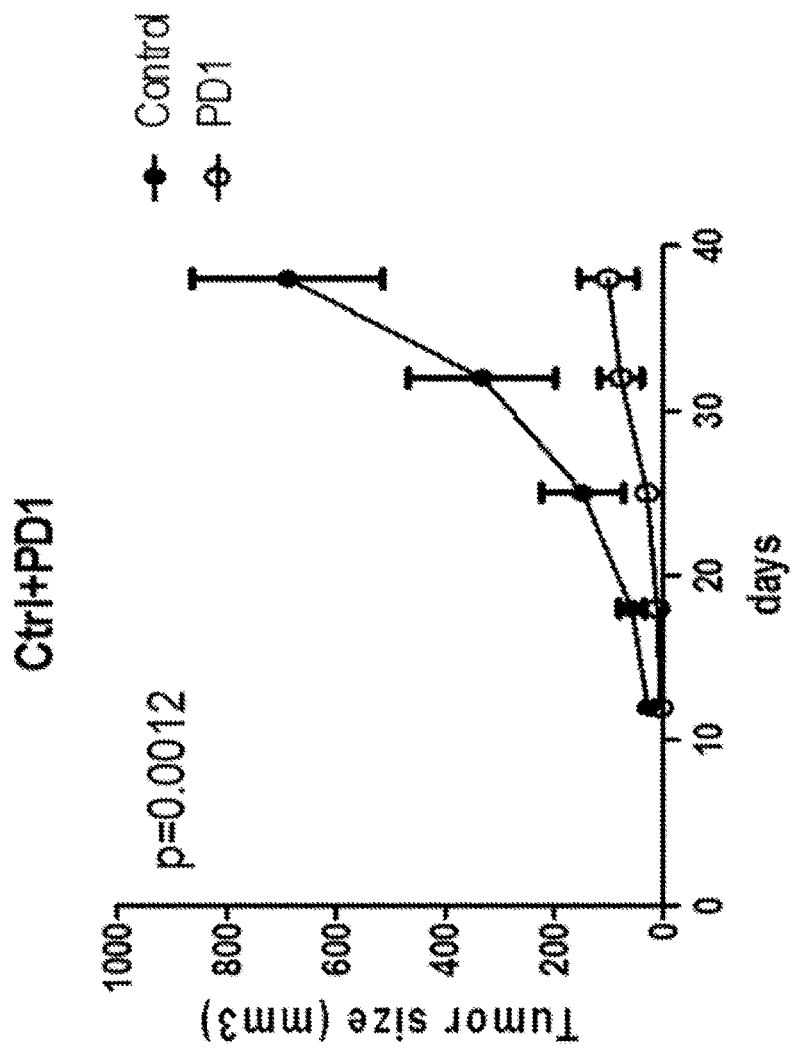
FIG. 17 is a graph showing the average inhibitory activity of the PD-1 antagonistic aptamer PD7 on the growth of lung cancer as compared to control mice.

Example 10: Anti-PD-1 Aptamer Inhibited Tumor Growth in an In Vivo Humanized Mouse Model A humanized lung cancer mouse model was used to demonstrate the inhibitory activity of anti-PD-1 aptamers described herein on the growth of lung cancer in vivo, using the PD-1 antagonistic aptamer PD7 (SEQ ID NO: 10) as an example. Briefly, human A549 lung cancer cells were subcutaneously transplanted into NOD mice at day 0 ($1.5 \times 10^6$ A549 cells per mouse). Human peripheral blood leukocytes (PBLs) were injected into mice one week after the A549 cells were transplanted into the mice. Mice were separated into the control, scrambled DNA treated, group (n=3; mouse 226, 233 and 239) or the PD-1 aptamer treated group (n=3; mouse 234, 235 and 240). The mice were administered 150 ul of 8 µM PD-1 aptamer or scrambled DNA control by intraperitoneal injection. A549 lung cell humanized mice were injected with the PD-1 aptamer or scrambled DNA control once a week for three weeks. A schematic representation of the treatment schedule is shown in FIG. 15. Tumor size was measured on days 25, 32 and 38 using an IVIS spectrum system. The tumor size in the PD7 treated mice (FIG. 16, panels A-D) was markedly decreased as compared to the tumor size of mice treated with scrambled DNA control (FIG. 16, panels E-H) at day 38 post tumor cell injection. An average of these data reveals a greater than 80% reduction in tumor size at day 38 when mice were treated with PD7 as compared to mice treated with the scrambled DNA control (FIG. 17). These data indicate that the anti-PD7 aptamer s can be used to treat human lung cancer.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A nucleic acid aptamer capable of binding programmed cell death protein 1 (PD-1), wherein the aptamer: comprises the nucleic acid sequence of

TCCCTACGGCGCTAACCTTCCATCTCCCATGCTTAGTCAAACATACGCC ACCGTGCTACAAC. (SEQ ID NO: 10)

2. The nucleic acid aptamer of claim 1, wherein the aptamer consists of the nucleic acid sequence of

TCCCTACGGCGCTAACCTTCCATCTCCCATGCTTAGTCAAACATACGCC ACCGTGCTACAAC. (SEQ ID NO: 10)

3. The nucleic acid aptamer of claim 1, wherein the nucleic acid aptamer is conjugated with polyethylene glycol (PEG).

4. The nucleic acid aptamer of claim 3, wherein the PEG is conjugated to the 3' end of the nucleic acid aptamer.

5. The nucleic acid aptamer of claim 3, wherein the PEG has a molecular weight ranging from 10 kDa to 30 kDa.

6. The nucleic acid aptamer of claim 3, wherein the PEG has a molecular weight of 20 kDa.

7. An anti-PD-1 aptamer dimer, comprising a first anti-PD-1 aptamer, a second anti-PD-1 aptamer, and a polymer moiety that links the first anti-PD-1 aptamer and the second anti-PD-1 aptamer, wherein both the first anti-PD-1 aptamer and the second anti-PD-1 aptamer comprise the nucleic acid sequence of SEQ ID NO:10.

8. The anti-PD-1 aptamer dimer of claim 7, wherein the polymer moiety is PEG.

9. The anti-PD-1 aptamer dimer of claim 8, wherein the PEG has a molecular weight ranging from 10 kDa to 30 kDa.

10. The anti-PD-1 aptamer dimer of claim 9, wherein the PEG has a molecular weight of 20 kDa.

11. The anti-PD-1 aptamer dimer of claim 7, wherein the first aptamer, the second aptamer, or both are linked to the polymer moiety via a linker.

12. The anti-PD-1 aptamer dimer of claim 11, wherein the linker comprises a polyT fragment.

13. The anti-PD-1 aptamer dimer of claim 12, wherein the polyT fragment contains 5-20 T residues.

14. A method for inhibiting programmed cell death protein 1 (PD-1), comprising administering to a subject in need thereof an effective amount of the nucleic acid aptamer of claim 1.

15. The method of claim 14, wherein the subject is a human patient having, suspected of having, or at risk for cancer.

16. The method of claim 14, wherein the cancer is melanoma, non-small cell lung cancer, colorectal cancer, or renal-cell cancer.

17. A method of enhancing immune activity in a subject, the method comprising administering to a subject in need thereof an effective amount of the nucleic acid aptamer of claim 1.

18. The method of claim 17, wherein the subject is a human patient having, suspected of having, or at risk for cancer.

19. The method of claim 18, wherein the cancer is melanoma, non-small cell lung cancer, colorectal cancer, or renal-cell cancer.

20. The method of claim of claim 17, wherein the subject is a human patient having or suspected of having HIV infection.

21. The method of claim 17, wherein the amount of the nucleic acid aptamer is effective in increasing T cell activation.

22. The method of claim 17, wherein the amount of the nucleic acid aptamer is effective in increasing the proliferation of CD8 positive T cells.

23. A method for inhibiting programmed cell death protein 1 (PD-1), comprising administering to a subject in need thereof an effective amount of the anti-PD-1 aptamer dimer of claim 7.

24. The method of claim 23, wherein the subject is a human patient having, suspected of having, or at risk for cancer.

25. The method of claim 24, wherein the cancer is melanoma, non-small cell lung cancer, colorectal cancer, or renal-cell cancer.

26. A method of enhancing immune activity in a subject, the method comprising administering to a subject in need thereof an effective amount of the anti-PD-1 aptamer dimer of claim 7.

27. The method of claim 26, wherein the subject is a human patient having, suspected of having, or at risk for cancer.

28. The method of claim 27, wherein the cancer is melanoma, non-small cell lung cancer, colorectal cancer, or renal-cell cancer.

29. The method of claim of claim 26, wherein the subject is a human patient having or suspected of having HIV infection.

30. The method of claim 26, wherein the amount of the anti-PD-1 aptamer dimer is effective in increasing T cell activation.

31. The method of claim 26, wherein the amount of the anti-PD-1 aptamer dimer is effective in increasing the proliferation of CD8 positive T cells.

* * * * *

SEQUENCE LISTING

```
<160> NUMBER OF SEQ ID NOS: 42

<210> SEQ ID NO 1
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 1 ccatctccc                                                            9

<210> SEQ ID NO 2
<211> LENGTH: 10
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
```

<223> OTHER INFORMATION: n is c or g

<400> SEQUENCE: 2 tatattgtnc                                                                                          10

<210> SEQ ID NO 3
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, c, or absent

<400> SEQUENCE: 3 gtacagttn                                                                                            9

<210> SEQ ID NO 4
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 4 gcactaca                                                                                             8

<210> SEQ ID NO 5
<211> LENGTH: 9
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: n is a, t, or absent

<400> SEQUENCE: 5 gtacatcan                                                                                            9

<210> SEQ ID NO 6
<211> LENGTH: 10
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, t, or absent
<220> FEATURE:
<221> NAME/KEY: misc_feature
<222> LOCATION: (10)..(10)
<223> OTHER INFORMATION: n is c, t, or absent

<400> SEQUENCE: 6 ngctactgtn                                                                                          10

<210> SEQ ID NO 7
<211> LENGTH: 13
<212> TYPE: DNA
<213> ORGANISM: Artificial Sequence
<220> FEATURE:
<223> OTHER INFORMATION: Synthetic Polynucleotide

<400> SEQUENCE: 7
ccatctcccg tcc                                                          13

<210> SEQ ID NO 8
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 8
cttccatctc ccatgcttag tcaaacatac                                        30

<210> SEQ ID NO 9
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 9
tgatcacaag aataactatc ccatctccct                                        30

<210> SEQ ID NO 10
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 10
tccctacggc gctaaccttc catctcccat gcttagtcaa acatacgcca ccgtgctaca       60
ac                                                                      62

<210> SEQ ID NO 11
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 11
tccctacggc gctaactgat cacaagaata actatcccat ctccctgcca ccgtgctaca       60
ac                                                                      62

<210> SEQ ID NO 12
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 12
tccctacggc gctaaccctc ccctagtata tattgtcctc gtctatgcca ccgtgctaca       60
ac                                                                      62

<210> SEQ ID NO 13
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 13
ccatctccca                                                              10

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
ccatctccca tttttttttt t                                                 21

<210> SEQ ID NO 15
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 15
tccctacggc gctaaccatc atcgatattg acacaaccat ctccctgcca ccgtgctaca       60
ac                                                                     62

<210> SEQ ID NO 16
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 16
tccctacggc gctaactcct gcatccatct ccctctgtta gttttggcca ccgtgctaca       60
ac                                                                     62

<210> SEQ ID NO 17
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 17
tccctacggc gctaacgtaa ttccatctcc ctcacagatt gctaacgcca ccgtgctaca       60
ac                                                                     62

<210> SEQ ID NO 18
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 18
tccctacggc gctaactcca tctcccttgt aacgttgctt cctcttgcca ccgtgctaca       60
ac                                                                     62

<210> SEQ ID NO 19
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 19
tccctacggc gctaaccgtc atcgttaata tattgtcctc gcataagcca ccgtgctaca    60
ac    62

<210> SEQ ID NO 20
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 20
tatattgtcc    10

<210> SEQ ID NO 21
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 21 gtacagtt    8

<210> SEQ ID NO 22
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 22 gtacatca    8

<210> SEQ ID NO 23
<211> LENGTH: 8
<212> TYPE: DNA
<213> ORGANISM: Artificial Sequence
<220> FEATURE:
<223> OTHER INFORMATION: Synthetic Polynucleotide

<400> SEQUENCE: 23 gctactgt    8

<210> SEQ ID NO 24
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 24
tccctacggc gctaacgtaa ttccatctcc ctcacagatt gctaacgcca ccgtgctaca    60
ac    62

<210> SEQ ID NO 25
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 25
tccctacggc gctaacttcc atctccttgc caccgtgcta caac    44

<210> SEQ ID NO 26
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 26
tccctacggc gctaactgcc accgtgctac aacatccta cggcgctaac tctccatctc    60
ccttgccacc gtgctacaac                                                80

<210> SEQ ID NO 27
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 27
tccctacggc gctaacccta cgcatccatc tccctatgta tgtcccgcca ccgtgctaca    60
ac                                                                   62

<210> SEQ ID NO 28
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 28
tccctacggc gctaacatcc atctccctgc caccgtgcta acatccct acggcgctaa     60 ctgccaccgt gctacaac                                                  78

<210> SEQ ID NO 29
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 29
tccctacggc gctaactatt ccatctccct cgccaccgtg ctacaac                  47

<210> SEQ ID NO 30
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 30
tccctacggc gctaactgat cacaagaata actatcccat ctccctgcca ccgtgctaca    60
ac                                                                   62

<210> SEQ ID NO 31
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 31
tctttccgcg gcggggggac tgggatcttc ttattgtgaa atcaaccccg tagga         55

<210> SEQ ID NO 32
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 32
tccctacggc gctaactcct gcatccatct ccctctgtta gaagctgcca ccgtgctaca    60
ac                                                                  62

<210> SEQ ID NO 33
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 33
tccctacggc gctaaccttc catctcccat gcttggtcaa acatacgcca ccgtgctaca    60
ac                                                                  62

<210> SEQ ID NO 34
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 34
tccctacggc gctaaccttc catctcccat gcttactcaa acatacgcca ccgtgctaca    60
ac                                                                  62

<210> SEQ ID NO 35
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 35
tccctacggc gctaacgaat tccatctccc tccactcaca gtcccggcca ccgtgctaca    60
ac                                                                  62

<210> SEQ ID NO 36
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 36
ttcctacggc gctaactcct gttcccctca caacacccct gggcaggcca ccgtgctaca    60
ac                                                                  62

<210> SEQ ID NO 37
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 37
tccctacggc gctaaccatc tccctgccac cgtgctacaa c        41

<210> SEQ ID NO 38
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 38
tccctacggc gctaactgtc ctcgcatccc atctccctac ggcgctaact gccaccgtgc    60
tacaac        66

<210> SEQ ID NO 39
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 39
tccctacggc gctaacgttg tgataagagg ttacaagttt ttcaccgcca ccgtgctaca    60
ac        62

<210> SEQ ID NO 40
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 40
tccctacggc gctaactgcc accgtgctac aacatcccta cggcgctaac catctccctg    60
ccaccgtgct acaac        75

<210> SEQ ID NO 41
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 41
tccctacggc gctaacctgg catttcctga ttgtttaacg cggccggcca tcgtgctaca    60
ac        62

<210> SEQ ID NO 42
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 42
tccctacggc gctaacaatg gtccatacta ccgacatcaa gtccccgcca tcgtgctaca    60
ac        62